United States Patent
Franzini et al.

(10) Patent No.: US 9,422,232 B2
(45) Date of Patent: Aug. 23, 2016

(54) REDUCTIVE RELEASE PROBES CONTAINING A CHEMOSELECTIVELY CLEAVABLE α-AZIDOETHER LINKER AND METHODS OF USE THEREOF

(75) Inventors: Raphael M. Franzini, Stanford, CA (US); Eric Todd Kool, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1253 days.

(21) Appl. No.: 13/383,135

(22) PCT Filed: Jul. 7, 2010

(86) PCT No.: PCT/US2010/041150
§ 371 (c)(1),
(2), (4) Date: Mar. 21, 2012

(87) PCT Pub. No.: WO2011/005821
PCT Pub. Date: Jan. 13, 2011

(65) Prior Publication Data
US 2012/0178086 A1    Jul. 12, 2012

Related U.S. Application Data

(60) Provisional application No. 61/270,647, filed on Jul. 9, 2009.

(51) Int. Cl.
| | | |
|---|---|---|
| C07C 247/04 | (2006.01) | |
| C12Q 1/68 | (2006.01) | |
| G01N 33/532 | (2006.01) | |
| A61K 49/00 | (2006.01) | |

(52) U.S. Cl.
CPC .......... *C07C 247/04* (2013.01); *A61K 49/0017* (2013.01); *C12Q 1/6818* (2013.01); *G01N 33/532* (2013.01)

(58) Field of Classification Search
CPC .......... G01N 33/532; C12Q 2563/107; C12Q 1/6818; C07C 247/04; A61K 49/0017
See application file for complete search history.

(56) References Cited

U.S. PATENT DOCUMENTS

| 2003/0060441 A1 | 3/2003 | Taylor et al. |
| 2006/0160081 A1 | 7/2006 | Milton et al. |
| 2006/0199192 A1 | 9/2006 | Kool et al. |

FOREIGN PATENT DOCUMENTS

| EP | 1860197 | 11/2007 |
| WO | 2006128138 | 11/2006 |
| WO | 2007008276 | 1/2007 |
| WO | 2007020457 | 2/2007 |
| WO | 2008036273 | 3/2008 |

OTHER PUBLICATIONS

Omura et al., Chemistry Letters, 2007, vol. 36, No. 4, p. 532-33.*
"Functional Groups," http://www.as.utexas.edu/astronomy/education/spring07/scalo/secure/AbioFunctionalGrpsVolIlRspect.pdf, as published online Jul. 17, 2013.*
Abe; et al. "Destabilizing universal linkers for signal amplification in self-ligating probes for RNA", JACS (Nov. 2004), 126(43):13980-13986.
Abe; et al. "A reduction-triggered fluorescence probe for sensing nucleic acids", Bioconjug Chem (Jun. 2008), 19(6):1219-1226.
Bently; et al. "Accurate whole human genome sequencing using reversible terminator chemistry", Nature (Nov. 2008), 456(7218):53-59.
Cai; et a. "Nucleic acid-triggered fluorescent probe activation by the Staudinger reaction", JACS (Dec. 2004), 126 (50):16324-16325.
Franzini; et al. "7-Azidomethoxy-coumarins as profluorophores for templated nucleic acid detection", Chembiochem (Dec. 2008), 9(18):2981-2988.
Franzini; et al. "Efficient Nucleic Acid Detection by Templated Reductive Quencher Release", JACS (Nov. 2009), 131(44):16021-16023.
Ju; et al. "Four-color DNA sequencing by synthesis using cleavable fluorescent nucleotide reversible terminators", PNAS (Dec. 2006), 103(52):19635-19640.
Pianowski; et al. "Fluorescence-based detection of single nucleotide permutation in DNA via catalytically templated reaction", Chem Commun (Oct. 2007), (37):3820-3822.
Sando; et al. "Quenched auto-ligating DNAs: Multicolor identification of nucleic acids at single nucleotide resolution", JACS (Feb. 2004), 126(4):1081-1087.

\* cited by examiner

*Primary Examiner* — Michael G Hartley
*Assistant Examiner* — Leah Schlientz
(74) *Attorney, Agent, or Firm* — Glenn J. Foulds; Bozicevic, Field & Francis LLP

(57) ABSTRACT

Probes comprising one or more selectively cleavable α-azidoether moieties are provided; and linkers comprising the one or more selectively cleavable α-azidoether moieties. The α-azidoether moiety will undergo a Staudinger reaction with a suitable reducing agent, resulting in cleavage. The probes find use in a variety of detection assays, e.g. specific polynucleotide binding assays, polypeptide binding assays, etc. The cleavable linkers are suitable for synthetic reactions, e.g. to prepare probes of the invention; in the synthesis of cleavable peptide conjugates; and the like.

16 Claims, 12 Drawing Sheets

REDUCTIVE RELEASE PROBES CONTAINING A CHEMOSELECTIVELY CLEAVABLE α-AZIDOETHER LINKER AND METHODS OF USE THEREOF

GOVERNMENT RIGHTS

This invention was made with Government support under grant GM068122 awarded by the National Institutes of Health. The Government has certain rights in the invention.

BACKGROUND OF THE INVENTION

Selectively cleavable linkers have found a number of uses in biochemistry, for example in reversible surface attachment of biomolecules; for pro-drug or targeted drug systems; in synthesis, and particularly in the synthesis of compounds for methods of detection, where the cleavable linker may release, for example, a fluorophore, or a fluorescence quencher moiety.

The detection of biomolecules through specific binding reagents is of great interest for a number of clinical research purposes. Analytes of interest include nucleic acids, such as mRNA, rRNA, genomic DNA, synthetic nucleic acids etc., and polypeptides, particularly antibodies and antigens, hormones, disease markers and the like. In such methods, a sensitive detection system is valuable for detecting minute quantities or concentrations of the analyte of interest. Detection systems of interest include fluorescence-based approaches, for example methods of detecting single nucleotide polymorphisms, genetic discrimination of pathogens, fluorescence activated cell sorting based on genetic variation, genetic identification of specific alleles in vivo, etc. Such systems are also applicable to polypeptide detection, e.g. in the analysis of tissue samples, in the detection of antibodies, pathogens, peptide markers and the like in tissue samples In particular, cleavable linkers that are triggered with mild, biologically compatible conditions are advantageous for detection of biomolecules in living cells, or samples where disruption of the system is undesirable. For example, detecting nucleic acids or polypeptides directly in living cells holds considerable promise for bioanalytical and clinical assays, as it bypasses time-consuming isolation and amplification steps. Particularly appealing are fluorescence-based approaches that shorten and simplify the protocol by obviating cell fixation and washing steps. Both molecular beacon-based probes and nucleic acid template reactive probes have recently been investigated for this purpose. DNA/RNA templated fluorescence activation, in particular, offers high selectivity, allowing for the discrimination of single nucleotide differences by fluorescence. Recent studies have utilized templated fluorogenic reactions to detect RNAs both in bacterial and mammalian cells.

The possibilities for useful detection and quantitation of specific genes and gene products are nearly endless. Genotyping methods are of interest for prenatal diagnosis; as well as detecting changes in genotype associated with disease, for example during oncogenesis. Genotyping methods also find use in pharmacogenomics, to determine an individual's profile for drug metabolism, including the likelihood of adverse reactions and responsiveness to treatment. Other important areas of research include analysis of mRNA for expression, alternative splicing and SNP variation. In addition to analysis of expression, and of sequence polymorphisms, there is significant interest in simply determining whether a target sequence is present in a sample, for example in the detection and identification of microbial species in clinical and environmental samples.

Evaluation of multiple chemical transformations for templated fluorescence activation has to date revealed several types of reactive probes, however only few are suitable for cellular nucleic acid detection. Quenched autoligation (QUAL) probes rely on an SN2-displacement of a fluorescence quencher to generate a fluorescence turn-on signal. Although QUAL probes allow sensing of highly expressed nucleic acids inside cells and have been used to distinguish between several closely related bacteria, they can be limited by slow ligation and by undesired reactions with endogenous nucleophiles. A second class of templated fluorescence activation probes uses the Staudinger reduction; such probes exhibit rapid kinetics and a high degree of bioorthogonality, beneficial for sensing in cells. However, the reported templated Staudinger schemes have involved the reduction of individually designed profluorophores, thus limiting their versatility and simplicity.

DNA probes comprising cleavable azidoether linkers, linkers that allow for preparation of these probes, and use thereof are described herein.

RELATED PUBLICATIONS

Milton et al. US Patent Appl. US20060160081A1, disclose nucleosides, nucleotides and nucleoside triphosphates containing fluorophores attached through cleavable connectors including α-azidoether. Ju et al., (2008) PNAS 105(27):9145-50.

Liu et al. WO 2007/020457, disclose modified nucleosides and nucleotides and uses thereof.

Seitz and Grossman, EP 1860197A1, describe a method for detecting target nucleic acids using DNA/RNA template mediated transfer reactions. Elements of the disclosure include a templated reaction between 2 probes, transfer of a tag or fluorophore between probes, detection of one of the probes, and a FRET based detection system. The transfer reaction involves a particular manipulation of nucleophilic and electrophilic groups, and not a phosphine reduction.

Kool et al., US 2006/0199192, disclose self-ligating oligonucleotide probes using fluorescence quencher leaving groups and its application to nucleic acid detection"; JACS 2004, 126 (4), 1081-7; "Quenched auto-ligating DNAs: Multicolor identification of nucleic acids at single nucleotide resolution"; US 2006199192, "Universal linker compositions for the release or transfer of chemical agents from a polynucleotide; JACS 2004, 126(43), 13980-6. "Destabilizing universal linkers for signal amplification in self-ligating probes for RNA". None of these probes involve an azidoether or a phosphine in the reaction.

The Staudinger reaction of aryl azides has been used in templated chemical reactions in the context of unmasking a fluorogenic probe. Examples include the DNA templated fluorescence activation of 7-azidocoumarin [Yumei, H. et al. WO 2006128138; Winssinger and Pianowski Chem. Commun., 2007, 3820-2 "Fluorescence-based detection of single nucleotide permutation in DNA via catalytically templated reaction."], 7-azidomethoxy coumarin [Franzini and Kool, ChemBioChem., 2008, 9(18), 2981-8, "7-Azidomethoxy-coumarins as profluorophores for templated nucleic acid detection."], azido-rhodamines [Abe et al., Bioconjugate Chem., "A reduction-triggered fluorescence probe for sensing nucleic acids."], azidomethoxy fluorescein [Furukawa et al. Bioconjugate Chem. 2009, 20, 1026-36 "Reduction-triggered fluorescent amplification probe for the detection of endogenous RNAs in living human cells"], and triphenylphosphine esters of fluorescein; [Cai et al., JACS 2004, 126(50), 16324-5, "Nucleic acid triggered fluorescent probe activation by the Staudinger reaction"]. None of these reports describe an azidoether or a cleavable linker to a quencher.

Yang et al. describe the use of multiple quenchers attached to nucleic acids in Molecular Beacon-type DNA probes [Yang et al. "Molecular Assembly of Superquenchers in Signaling Molecular Interactions," J. Am. Chem. Soc., 2005, 127 (37), pp 12772-12773; Tan et al. WO/2006/002167, "Multi-acceptor molecular probes and applications thereof"]. Grossmann et al. use the superquenching approach in triplex molecular beacons [Grossmann et al. "Triplex Molecular Beacons as Modular Probes for DNA Detection," Angew. Chem. Int. Ed. 2007, 46, 5223-5225]. The quenchers are not released in these probe designs and there is no bond-cleaving reaction.

SUMMARY OF THE INVENTION

Probes comprising one or more selectively cleavable α-azidoether linkers are provided. The α-azidoether moiety will undergo reductive cleavage when exposed to a suitable reducing agent, e.g. a phosphine. Probes of the invention generally comprise a specific binding moiety, e.g. a polynucleotide, antigen, antibody moiety, minor groove binder etc.; at least one detection moiety, e.g. a fluorophore, a fluorophore quencher etc.; and at least one α-azidoether cleavable moiety. In some embodiments, a quencher and fluorophore are linked through an α-azidoether cleavable moiety. In some embodiments, two or more quenchers are linked to a fluorophore-labeled polynucleotide via one, two or more α-azidoether cleavable moieties. In some embodiments, probes of the invention are multivalent, i.e., the probe includes multiple detection moieties linked to a specific binding moiety. In some embodiments, probes of the invention are monovalent, i.e., the probe includes a single detection moieties linked to a specific binding moiety. The probes find use in a variety of detection assays, e.g. sequence specific polynucleotide binding assays, polypeptide binding assays, detection of single nucleotide polymorphisms in real time PCR applications, genetic discrimination of pathogens, analysis of pathological tissue samples, fluorescence activated cell sorting based on genetic variations, genetic identification of specific alleles in vivo, etc. The cleavable linkers are suitable for synthetic reactions, e.g. to prepare probes of the invention; in the synthesis of cleavable oligonucleotide conjugates; in the synthesis of cleavable peptide conjugates; in the synthesis of reversible surface attachment conjugates; and the like.

Methods are provided for detecting a target polynucleotide sequence in a sample, using selectively cleavable probes of the invention. In some embodiments, the method includes a first probe containing a polynucleotide-binding region labeled with a fluorophore that is connected to a quencher via a selectively cleavable α-azidoether moiety. When the first probe hybridizes to a region of the target oligonucleotide sequence adjacent to a second hybridized probe that contains a suitable reducing agent, the linker is cleaved, and a quencher is released. A fluorescent signal is generated by the cleaved first probe. In other embodiments, the method includes a first probe containing a polynucleotide-binding region labeled with a fluorophore that is connected to two quenchers via two selectively cleavable α-azidoether moieties. When the first probe hybridizes to a region of the target oligonucleotide sequence adjacent to a second hybridized probe that contains a suitable reducing agent, the first α-azidoether moiety is cleaved, and the first quencher is released. Dissociation of the second hybridized probe that is oxidized in the first cleavage reaction, and hybridization of a further second probe, leads to cleavage of the second α-azidoether moiety and release of the second quencher to generate the fluorescent signal. In some embodiments of the invention, a set of probes is provided for use in such methods. The compositions and methods described herein can be used in both in vitro and in vivo applications.

In some embodiments the selectively cleavable α-azidoether moiety of the invention has the structure of formula (I): (Note that the ether could be reversed, with N3 on the left instead of the right.)

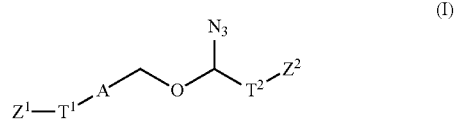

(I)

where A is an is an aromatic ring of 5 or 6 carbons, optionally substituted with one or more lower alkyl, halogen, hydroxyl, amino; etc.

where $T^1$ and $T^2$ are tethers; $T^1$ is at the ortho, para or meta position, usually para or meta; and $Z^1$ and $Z^2$ are independently a functional group, a specific binding moiety or a detection moiety.

In some embodiments, the probe of the invention has the structure of formula (II):

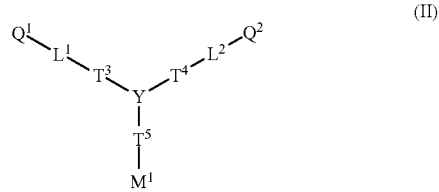

(II)

where $T^3$, $T^4$ and $T^5$ are tethers;
Y is carbon or nitrogen;
$L^1$ and $L^2$ are selectably cleavable α-azidoether moieties;
$Q^1$ and $Q^2$ are detection moieties; and
$M^1$ is a specific binding moiety.

DEFINITIONS

Figure 1:
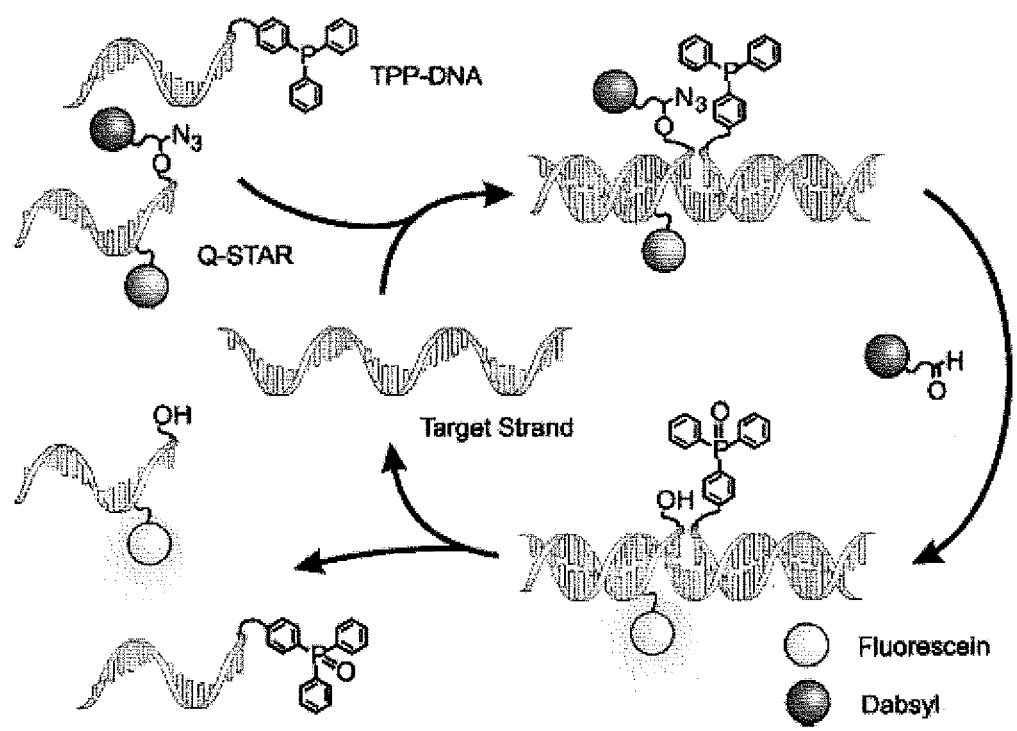
FIG. 1. Detection of nucleic acids by templated fluorescence activation of Q-STAR probes.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing those components that are described in the publications that might be used in connection with the presently described invention.

As used herein, compounds which are "commercially available" may be obtained from standard commercial sources including Acros Organics (Geel Belgium), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Invitrogen (Carlsbad, Calif.), Applied Biosystems, Inc. (Foster City, Calif.), Glen Research (Sterling, Va.), Biosearch Technologies (Novato, Calif.), Anaspec (Fremont, Calif.) and Berry & Associates (Dexter, Mich.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified through various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

It should also be understood that any of the moieties defined herein may be substituted with a variety of substituents, and that the respective definitions are intended to include such substituted moieties within their scope.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$. Typical substituents include, but are not limited to, —X, —R$^8$ (with the proviso that R$^8$ is not hydrogen), —O—, =O, —OR$^8$, —SR$^8$, —S$^-$, =S, —NR$^8$R$^9$, =NR$^8$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^8$, —OS(O$_2$)O$^-$, —OS(O)$_2$R$^8$, —P(O)(O—)$_2$, —P(O)(OR$^8$)(O), —OP(O)(OR$^8$)(OR$^9$), —C(O)R$^8$, —C(S)R$^8$, —C(O)OR$^8$, —C(O)NR$^8$R$^9$, —C(O)O$^-$, —C(S)OR$^8$, —NR$^{10}$C(O)NR$^8$R$^9$, —NR$^{19}$C(S)NR$^8$R$^9$, —NR$^{11}$C(NR$^{10}$)NR$^8$R$^9$ and —C(NR$^{19}$)NR$^8$R$^9$, where each X is independently a halogen.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

"Tether", for example T$^1$ and T$^2$, as used in the structures herein, refers to a linking moiety of up to about 20 atoms in length. A tether may be a single bond or a chain of from about 1 to about 20 atoms in length, for example of about 1, 2, 3, 4, 5, 6, 8, 10, 12, 14, 16, 18 or 20 carbon atoms in length, where the tether backbone optionally includes one or more sulfur, nitrogen and oxygen heteroatoms, which tether may comprise one, two, three, five, seven or more backbone heteroatoms. The bonds between backbone atoms may be saturated or unsaturated, usually not more than one, two, or three unsaturated bonds will be present in a tether backbone. Each of the backbone atoms may be substituted or unsubstituted, for example with an alkyl, aryl or alkenyl group. A tether may include, without limitations, oligo(ethylene glycol); ethers, thioethers, tertiary amines, alkyls, which may be straight or branched, e.g., methyl, ethyl, n-propyl, 1-methylethyl(iso-propyl), n-butyl, n-pentyl, 1,1-dimethylethyl(t-butyl), and the like. The tether backbone may include a cyclic group, for example, an aryl, a heterocycle or a cycloalkyl group, where 2 or more atoms, e.g., 2, 3 or 4 atoms, of the cycle are included in the linear backbone.

"Quencher" refers to any fluorescence-modifying group that can alter at least partly the light emitted by a fluorescent group. A probe having a quencher may also comprise one or more donor fluorophores. The quencher may alter the light emission by the fluorescent group by any known mechanism including without limitation resonance energy transfer (e.g. Förster resonance energy transfer), reductive electron transfer, oxidative electron transfer, excited state reactions, complex formation, collision quenching, electron exchange (e.g. Dexter energy exchange), etc. The quencher may or may not be a fluorescent molecule, it being sufficient that the quencher prevents radiative dexcitation of the excited fluorophore. A fluorophore-quencher pair may be chosen such that the quencher can donate or accept charge to or from the excited-state fluorophore. Any fluorescence quencher can be used, for example the quencher can be a diazo-dye e.g. DABSYL (dimethylamino-azobenzene-sulfonyl) group, DABCYL (dimethylamino-azobenzene-carboxy), BLACK HOLE QUENCHERS™, DANSYL (5-dimethylaminonaphthalene-sulfonyl); DIMAPDABSYL ((p-dimethylamino-phenylazo) azobenzenesulfonyl), any of which may comprise substituents such as amino, dialkylamino, nitro, fluoro, and cyano groups; anthraquinone, nitrothiazole, viologen, and nitroimidazole compounds; rhodamine dyes (e.g., tetramethyl-6-carboxyrhodamine (TAMRA)); ROX; cyanine; coumarin; BODIPY dyes; fluorescein dyes; ALEXA™ dyes; QXL™ dyes; and the like.

Where a biomolecule of the invention comprises a quencher, the probe or linker may further comprise one or more donor or acceptor fluorophore(s), which is quenched prior to the release of the quencher. Any known method of incorporating a fluorophore into a modified probe can be used. It is preferred that a fluorophore be located close to the quencher, but this is not required. The fluorophore can generally be located at any distance from the quencher sufficient to permit detection by monitoring the change in fluorescent properties. For example, the fluorophore can be located 1, 2, 3 or more, and usually will be not more than about 10, 15 or 20 nucleotides away from the quencher.

The efficiency of quenching (i.e. the unquenched fluorescence with the fluorescence quenching group absent divided by the quenched fluorescence with the fluorescence quenching group present) may be at least about 2 fold, at least about 3 fold, at least about 4 fold, at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, at least about 100 fold, at least about 200 fold, at least about 300 fold, at least about 400 fold, at least about 500 fold, at least about 600 fold, at least about 700 fold, at least about 800 fold, at least about 900 fold, at least about 1000 fold, at least about 2000 fold, at least about 3000 fold, at least about 4000 fold, or at least about 5000 fold.

"Fluorophore" refers to a molecule that, when excited with light having a selected wavelength, emits light of a different wavelength, which may emit light immediately or with a delay after excitation. Fluorophores, include, without limitation, fluorescein dyes, e.g., 5-carboxyfluorescein (5-FAM), 6-carboxyfluorescein (6-FAM), 2',4',1,4,-tetrachlorofluorescein (TET), 2',4',5',7',1,4-hexachlorofluorescein (HEX), and 2',7'-dimethoxy-4',5'-dichloro-6-carboxyfluorescein (JOE); cyanine dyes, e.g. Cy3, CY5, Cy5.5, QUASAR™ dyes etc.; dansyl derivatives; rhodamine dyes e.g. 6-carboxytetramethylrhodamine (TAMRA), CAL FLUOR™ dyes, tetrapropano-6-carboxyrhodamine (ROX). BODIPY fluorophores, ALEXA™ dyes, Oregon Green, pyrene, perylene, benzopyrene, squarine dyes, coumarin dyes, luminescent transition metal and lanthanide complexes and the like. The term fluorophores includes excimers and exciplexes of such dyes.

Detection "in vivo" refers to detection of analytes in living cells, tissues or organisms. Cells can be obtained from cell cultures or from test animals or patient sources; cells include without limitation bacterial cells, mammalian cells, embryonic or somatic stem cells, spermatocytes, yeast cells, erythrocytes, leukocytes etc. Organisms may include test animals or patients. The methods of the invention also find use in the analysis of intact cells, tissue samples or organisms that are no longer living, which may be referred to as ex vivo detection. Such samples are optionally fixed, permeabilized, etc., as known in the art, although such processing is not necessary.

DETAILED DESCRIPTION OF THE EMBODIMENTS

Linkers comprising a selectively cleavable α-azidoether moiety are provided; and probes comprising one or more of the selectively cleavable α-azidoether linkers. The α-azidoether moiety will undergo reductive cleavage induced by a suitable reducing agent. The probes find use in a variety of detection assays. The cleavable linkers are suitable for synthetic reactions.

"Cleavable moiety" refers to a group that is cleaved under conditions of interest, and as used herein specifically references a cleavable α-azidoether moiety. A cleavable moiety of the present invention is stable, e.g. to physiological conditions, until it is contacted with a reagent capable of triggering cleavage of the cleavable linker. For example, the α-azidoether moiety can react with a suitable reducing agent, such as alkyl or aryl phosphine, in a reaction (i.e., a Staudinger reaction) that results in cleavage of the linker. In such a reaction, reduction of the α-azidoether moiety by the phosphine gives an iminophosphorane intermediate that is readily hydrolyzed.

In some embodiments, the selectively cleavable α-azidoether moiety of the invention may be part of a cleavable linker or a probe. In some embodiments, two or more selectively cleavable α-azidoether moieties of the invention may be part of a branched cleavable linker or probe. The α-azidoether moiety is of the structure of formula (I):

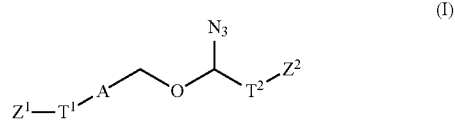

(I)

where A is an is an aromatic ring of 5 or 6 carbons, optionally substituted with one or more of a lower alkyl, halogen, hydroxyl, amino, etc.;

$T^1$ and $T^2$ are tethers; $T^1$ is at the ortho, para or meta position, usually para or meta; and $Z^1$ and $Z^2$ are independently a functional group, a specific binding moiety or a detection moiety.

Cleavage conditions are conditions suitable to trigger the cleavage of a cleavable moiety, e.g., a cleavable linker or a probe containing a cleavable linker. For an α-azidoether containing cleavable linker or probe, cleavage occurs through a reduction reaction. For example, the α-azidoether moiety will react with a suitable reducing agent, followed by hydrolysis of the resulting α-amino ether. Suitable methods for reduction of the α-azidoether moiety include, without limitation: Lewis acid/silane reductions, $InCl_3/Et_3SiH$ (e.g. Benati, et al. Org. Lett., 2006, 8, 2499-2502.); Pd/C catalyzed hydrogenolysis (e.g. Sajiki, Tetrahedron Lett., 1995, 36, 3465-

3468); (Me₃Si)₃SiH based reductions (e.g., Postigo et al., Org. Lett., 2007, 9, 5159-5162), or the like.

In some cases, the reduction of the α-azidoether occurs in aqueous solution or in a mixture of water and a suitable co-solvent. Suitable methods for reduction of the α-azidoether in water or water/co-solvent mixtures include, without limitation: hydride reductions e.g. $NaBH_4/CoCl_2$ (e.g. F. Fringuelli, Synthesis, 2000, 5, 646-50), silane reductions e.g. $(Me_3Si)_3SiH$/mercaptoethanol (e.g. A. Postigo, Org. Lett., 2007, 9, 5159-62), thiols or dithiols (e.g. J. E. Reardon, J. Biol. Chem., 1994, 269, 15999-16008), or the like.

In particular embodiments, the reduction of the α-azidoether moiety involves a Staudinger reaction in which the combination of an azide with a phosphine or phosphite reducing agent produces an iminophosphorane intermediate. Combined with the hydrolysis of the aza-ylide to produce a phosphine oxide and an amine, this reaction is a mild method of reducing an azide to an amine; likewise the Staudinger reaction of α-azidoether moieties leads to cleavage of the α-azidoether. Triphenylphosphine, or the like, is commonly used as the reducing agent in organic Staudinger reactions, yielding triphenylphosphine oxide as a side product. In addition, in biological applications the water soluble TCEP (tris(2-carboxyethyl)phosphine), or the like, is also commonly used. Many other substituted alkyl and substituted aryl phosphine reagents are also commercially available, that in some embodiments may be used in probes and methods of the present invention, for example, 3-carboxyphenyl-diphenylphosphine, 2-carboxyphenyl-diphenylphosphine, a substituted cyclohexyldiphenylphosphine, a substituted dicyclohexyl (2-methylphenyl)phosphine, a substituted diethylphenylphosphine, a substituted triethylphosphine, a tris(2-carboxyethyl) phosphine and a substituted tributylphosphine.

In some cases, probes of the present invention contain a reducing agent, for example, a phosphine reducing agent attached to a specific binding moiety e.g. polynucleotide, polypeptide, protein, antigen, antibody, minor grove binder etc., via one of the three organic substituents around the phosphorus of the phosphine. For example, 4-carboxyphenyl-diphenylphosphine may be attached to a probe via coupling to the 4-carboxy group. Reducing agents other than phosphines may be attached to specific binding reagents for the reductive cleavage of α-azidoether linker and probes prepared thereof, including without limitation: organic dithiols, organic selenols, organic diselenols, and organic compounds containing a thiol and a selenol functional group.

"Cleavable linker" refers to a linker containing a cleavable moiety, usually a reactive linker, which may find use in synthetic reactions. For the purposes of the present invention, a cleavable linker comprises a cleavable moiety of formula (I), where $T^1$ and $T^2$ are tethers and where A is an is an aromatic ring of 5 or 6 carbons, optionally substituted with one or more of a lower alkyl, halogen, hydroxyl, amino; etc.; $Z^1$ and $Z^2$ are functional groups suitable for use in synthetic reaction.

In some embodiments $Z^1$ and $Z^2$ are independently selected from the group consisting of amino, carbonylamino, aminocarbonylamino, aminocarbonyloxy, carbonate, anhydride, alkynyl, azido, azidocarbonylamino, azidocarbonyloxy, chlorocarbonylamino, chlorocarbonyloxy, hydrazino, hydrazido, aminoxycarbonyl, aminoxy, aziridine, epoxide, haloalkyl, hydroxyl, keto, carbonyl, carboxyl, aldehyde, silylether, arylether, arylthioether, tosyl, thiocarbonyl, thio, a disulfide, isocyanate, isothiocyanate, maleimido, iodoacetyl, N-hydroxysuccinimide, chlorosulfo, sulfonamido, phosphodiester, fluorophosphonate, alkyl-S(O)—, aryl-S(O)—, alkyl-S(O)₂—, aryl-S(O)₂, vinyl sulfone, and protected versions thereof.

In certain embodiments the cleavable linker comprises a cleavable moiety of formula (III): (azide can also be on the left of the oxygen)

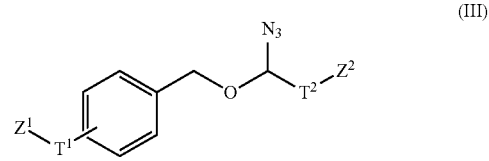

where $T^1$, $T^2$, $Z^1$ and $Z^2$ are as defined above.

In certain embodiments the cleavable linker comprises a cleavable moiety of formula (III), where $Z^1$ is a carboxyl group and $Z^2$ is an amino group, such that the cleavable linker is of the structure for formula (IV):

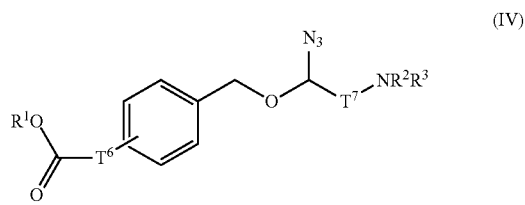

where $R^1$, $R^2$ and $R^3$ are independently selected from the group consisting of hydrogen, an alkyl, an aryl, a heterocycle, an amino protecting group and a carboxyl protecting group; and $T^6$ and $T^7$ may be independently absent or present; and when present are independently an alkyl of from 1 to 6 carbons in length.

In certain embodiments, the cleavable linker is of the structure of formula (IV), where $R^1$ is methyl and $R^2$ and $R^3$ are hydrogen. In certain embodiments, in formula (IV), $R^1$ is hydrogen; one of $R^2$ and $R^3$ is an amino protecting group (e.g., a trityl protecting group); and the other of $R^2$ and $R^3$ is hydrogen.

In particular embodiments, the cleavable linker is of the structure of formula (V):

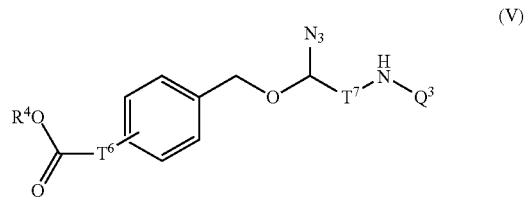

where $T^6$ and $T^7$ are as defined above;

$Q^3$ is a detection moiety, particularly a fluorophore or a quencher; and $R^4$ is hydrogen, an alkyl, a carboxyl protecting group, or a carboxyl activating group. In particular embodiments, the cleavable linker is of the structure of formula (V), where $Q^3$ is a quencher and $R^4$ is hydrogen.

In certain embodiments, the cleavable linker is of the structure of one of formulas (VIa) and (VIb):

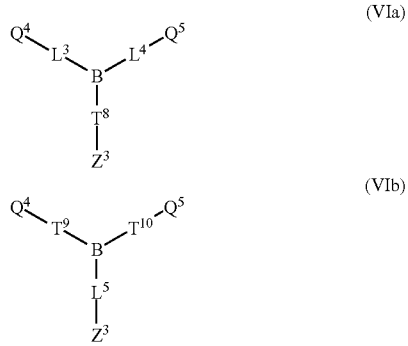

(VIa)

(VIb)

where $Q^4$ and $Q^5$ are detectable moieties;
$Z^3$ is a functional group or a specific binding moiety;
$L^3$, $L^4$ and $L^5$ are selectively cleavable α-azidoether moieties;
each B is a branching moiety (e.g., a carbon, a nitrogen, an amino acid derivative or a dendrimer); and
$T^8$, $T^9$ and $T^{19}$ are tethers.

In particular embodiments, the cleavable linker is of the structure of formula (VII):

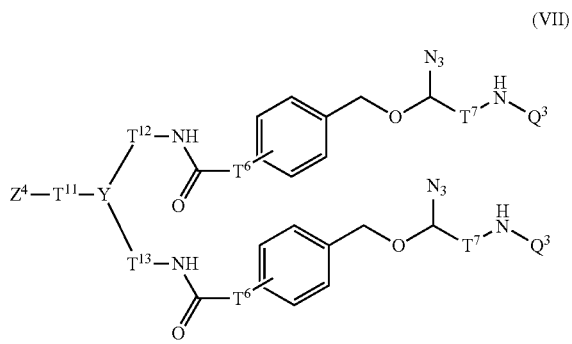

(VII)

where $T^6$, $T^7$ and $Q^3$ are as defined above;
$Z^4$ is a functional group;
$T^{11}$, $T^{12}$ and $T^{13}$ are tethers; and
Y is carbon or nitrogen.

Cleavable linkers of the invention may be used as a bifunctional linker, for example, the cleavable linker may be used to connect a reporter group such as a quencher, a fluorophore, a drug, a prodrug, a radioisotope, a metal nanoparticle, a biotin, a ligand, a tag, an enzyme, a coenzyme, a spin label, a redox-active reagent, a chemical reagent, a solid support, or the like; to a biomolecule such as an antibody, a cell, a polynucleotide, a peptide, a ligand, a protein, an enzyme, a receptor, an antigen, or fragment or analog thereof. For example, the cleavable linker may be used to connect a drug or prodrug to a ligand or other drug delivery system for the purpose of delivering the drug or prodrug to, for example, a cell receptor. In certain embodiments, the cleavable linker may be used in a probe where cleavage is triggered after binding to a specific target(s), for example, a nucleic acid, an enzyme, an antibody or receptor target.

A cleavable linker may be utilized in synthesis of a probe by connecting two or more moieties, such as 2, 3, 4 or more moieties, independently selected from specific binding moieties, detection moieties, solid substrates, reporter groups, ligands, and the like; where the two or more moieties may be connected in series, or via a branched linker containing one, two or more selectively cleavable α-azidoether linkers; where optionally a moiety may also be attached via another linker, e.g., a photocleavable linker, an acid cleavable linker, a base cleavable linker, a non-cleavable linker, or the like. A cleavable linker of the present invention may be hetero-bifunctional, where the linker contains orthogonal functional groups, or it may be homobifunctional where the functional groups have similar orthogonality.

A drug or prodrug, may include chemotherapeutic agents for neoplastic tissues, anti-inflammatory agents for ischemic or inflamed tissues, hormones or hormone antagonists for endocrine tissues, ion channel modifiers for cardiovascular or other tissues, and neuroactive agents for the central nervous system. Exemplary of pharmaceutical agents suitable for this invention are those described in The Pharmacological Basis of Therapeutics, Goodman and Gilman, McGraw-Hill, New York, N.Y., (1993) under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference.

The term "prodrug" refers to a precursor or derivative form of a pharmaceutically active substance that is less active than the parent drug and is capable of being converted into the more active parent form. Use of prodrugs allows the modulation of onset and/or duration of action of a biologically-active compound in vivo. A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

Prodrugs of interest include, but are not limited to, phosphate-containing prodrugs, thiophosphate-containing prodrugs, sulfate-containing prodrugs, peptide-containing prodrugs, D-amino acid-modified prodrugs, glycosylated prodrugs, P-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Glucuronide prodrugs can be enzymatically converted to active agents by beta-glucuronidase. Other prodrugs are based on ester or phosphate linkages have been reported.

In some embodiments, a cleavable linker is attached to a solid support (for example: beads, membrane, 96-well plate, array substrate, filter paper and the like) directly or indirectly. Suitable solid supports may have a variety of forms and compositions and derive from naturally occurring materials, naturally occurring materials that have been synthetically modified, or synthetic materials. Examples of suitable support materials include, but are not limited to, CPG, silicas, teflons, glasses, polysaccharides such as cellulose, nitrocellulose, agarose (e.g., Sepharose® from Pharmacia) and dextran (e.g., Sephadex® and Sephacyl®, also from Pharmacia), polyacrylamides, polystyrenes, polyvinyl alcohols, copolymers of hydroxyethyl methacrylate and methyl methacrylate, and the like.

The linkers of the invention are useful in providing a cleavable attachment of a biomolecule to a substrate. By "solid substrate" or "solid support" is meant any surface to which the probes of the invention are attached. A variety of solid supports or substrates are suitable for the purposes of the invention, including both flexible and rigid substrates. By flexible is meant that the support is capable of being bent, folded or similarly manipulated without breakage. Examples of flexible solid supports include nylon, nitrocellulose, polypropylene, polyester films, such as polyethylene terephthalate, etc. Rigid supports do not readily bend, and include glass, fused silica, quartz, acrylamide; plastics, e.g. polytetrafluoroethylene, polypropylene, polystyrene, polystyrene and sulfonated polystyrene-divinyl benzene, quaternized product of chloromethylated polystyrene-divinyl benzene, PEG-polystyrene, PEG, polycarbonate, and blends thereof, and the like; metals, e.g. gold, platinum, silver, and the like; etc. The substrates can take a variety of configurations, including planar surfaces, filters, fibers, membranes, beads, particles, dipsticks, sheets, rods, etc.

"Probe" refers to a molecule that is capable of binding specifically to a target analyte, e.g., a polynucleotide, a peptide, a protein, an antibody, antigen, or fragment or analog thereof. Probes often include a detection moiety, e.g. a fluorophore, quencher, radioisotope, enzyme, a tag, a metal nanoparticle, etc. Fluorophores and quenchers are of particular interest. Probes of the invention comprise a selectively cleavable α-azidoether moiety, where in some embodiments the probe has the structure of formula (VIIIa) or (VIIIb):

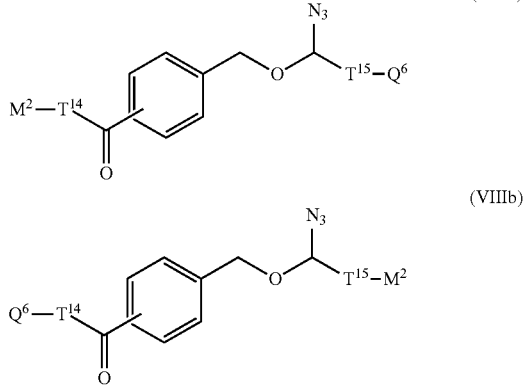

where $T^{14}$ and $T^{15}$ are tethers; $Q^6$ is a detection moiety, and $M^2$ is a specific binding moiety.

The term "specific binding moiety" as used herein refers to a member of a specific binding pair, i.e. two molecules where one of the molecules through chemical or physical means specifically binds to the other molecule. The complementary members of a specific binding pair are sometimes referred to as a ligand and receptor, although two complementary polynucleotide sequences (including nucleic acid sequences used as probes and capture agents in DNA hybridization assays) are also specific binding pairs, as are antibody and antigen, peptide-MHC antigen and T cell receptor pairs; etc. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present.

Immunological specific binding pairs include antigens and antigen specific antibodies or T cell antigen receptors. Recombinant DNA methods or peptide synthesis may be used to produce chimeric, truncated, or single chain analogs of either member of the binding pair, where chimeric proteins may provide mixture(s) or fragment(s) thereof, or a mixture of an antibody and other specific binding members. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

In certain embodiments, the directionality of the cleavable linker may be reversed, such that $M^2$ and $Q^6$ are attached at the opposite ends, as shown in formulas (VIIIa) and (VIIIb). In some embodiments, the specific binding moiety is a single stranded polynucleotide, and the detection moiety is a fluorescence quencher. In other embodiments, the specific binding moiety is a peptide, a protein an antibody, or a fragment thereof.

In certain embodiments, a probe of the present invention is of the structure of formula (Va), where the specific binding moiety is a 3'-bound or a 5' bound polynucleotide, the detection moiety is a quencher, such that the probe has a structure of formula (IX):

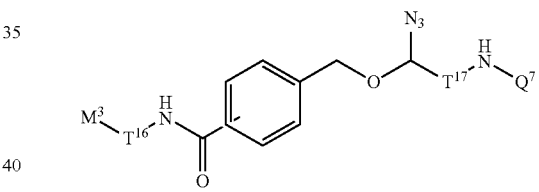

where $Q^7$ is a quencher; $M^3$ is a polynucleotide; and $T^{16}$ and $T^{17}$ are independently selected tethers. In some embodiments, $M^3$ is a polynucleotide that includes a fluorophore, usually where the fluorophore is selected to be quenched by $Q^7$. Alternatively, $Q^7$ can be a fluorophore and $M^3$ a polynucleotide that includes a quencher.

"Oligonucleotide", or "polynucleotide" means either DNA, RNA, single-stranded or double-stranded, and derivatives thereof, including, but are not limited to: 2'-position sugar modifications e.g. 2'-OMe RNA, 2'-F RNA; phosphate modifications e.g. phosphorothioates, phosphorodithioates, phosphonates; propynyl additions, for example at the at the 5 position of pyrimidines; 5-position pyrimidine modifications, 7- or 8-position purine modifications, modifications at exocyclic amines, 5-methyl cytosine; 5 bromo-cytosine; alkynyl uridine and cytosine; substitution of 4-thiouridine, substitution of 5-bromo or 5-iodo-uracil; backbone modifications, including peptide nucleic acids (PNA), locked nucleic acids (LNA), etc., methylations, morpholino derivatives; phosphoroamidate derivatives; stabilizing bases e.g. G-clamp, 2,6-diaminopurine; fluorophore modifications; unusual base-pairing combinations such as the isobases isocytidine and isoguanidine and the like. Derivatives can also include 3' and 5' modifications such as capping, addition of a tether with a functional group, biotinylation, cholesterol, addition of a fluorophore. Individual nucleotide residues within the polynucleotide sequence may be modified, for example, modified at the nucleobase, or on the backbone, to include a group such as a fluorophore or a biotin, etc.

In certain embodiments, a probe of the invention has the structure of formula (II):

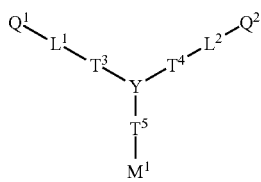

(II)

where $T^3$, $T^4$ and $T^5$ are tethers;
Y is carbon or nitrogen;
$L^1$ and $L^2$ are selectably cleavable α-azidoether moieties;
$Q^1$ and $Q^2$ are detection moieties; and
$M^1$ is a specific binding moiety.

In certain embodiments, in formula (II), the specific binding moiety $M^1$ is a single stranded polynucleotide that includes a fluorophore, and the detection moieties $Q^1$ and $Q^2$ are fluorescence quenchers, where usually the fluorophore is selected to be quenched by $Q^1$ and $Q^2$. In other embodiments, the specific binding moiety is a peptide, a protein, an antibody, or a fragment thereof.

In certain embodiments, a probe of the invention has the structure of formula (X):

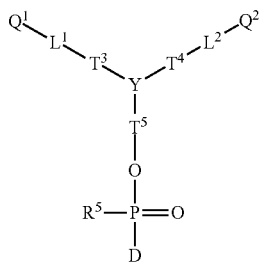

(X)

where $T^3$, $T^4$, $T^5$, Y, $L^1$, $L^2$, $Q^1$ and $Q^2$ are defined above;
D is a polynucleotide; and
$R^5$ is $OR^6$, $SR^6$, $O^-$, $S^-$ or a lower alkyl, which may be linear or branched; where $R^6$ is methyl or other lower alkyl, straight or branched, or beta-cyanoethyl.

In certain embodiments, the tethers (e.g., $T^1$ to $T^{23}$) are independently selected from one of the following structures, or a substituted version thereof:

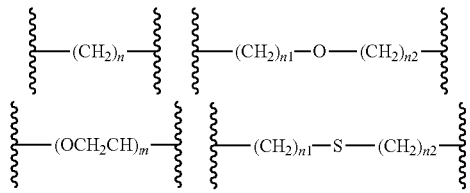

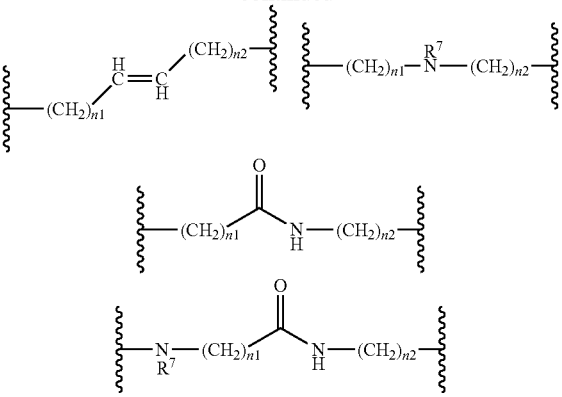

where n is an integer from 1 to 20;
$n_1$ and $n_2$ are independently selected integers from 1 to 20;
where $n_1+n_2$ is usually not more than about 20;
m is an integer from 1 to 7; and
$R^7$ is selected from hydrogen and an alkyl, usually branched or linear lower alkyl.

In some embodiments, the probe of the invention is of the structure of formula (XI):

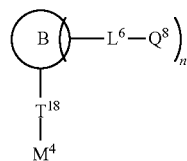

(XI)

where $M^4$ is a specific binding moiety;
$T^{18}$ is a tether;
n is 2, 3, 4, 5, or 6;
B is a branching moiety (e.g. a carbon atom where n can be 2, or 3; a nitrogen atom where n is 2); an amino acid derivative such as a lysine derivative; or a dendrimer) that provides for linkage of multiple $Q^8$ groups to $M^4$; and
each $L^6$ is independently a cleavable α-azidoether moiety, and each $Q^8$ is independently a detection moiety. In particular embodiments, in formula (XI), n is 3; each $Q^8$ is a quencher; and $M^4$ is a polynucleotide that includes a fluorophore, usually selected to be quenched by the $Q^8$ quenchers.

Reference may be made herein to the hybridization, or potential for hybridization, of probe sequences to a target sequence. For example, the polynucleotide portion of a first and second probe may hybridize, respectively, to "neighboring" sites on the target through base complementarity. Two such sites, when aligned on the target polynucleotide sequence, are considered to be "neighboring" if the sites are contiguous on the target; are separated by one, two, three or more bases on the target; or overlap by one, two three or more bases on the target. In another example, the polynucleotide portions of a first and a second probe may hybridize to each other either independently or in conjunction with binding of the probes to a common target e.g. a polynucleotide or a protein. In another example, the polynucleotide portions of a first and a second probe bind to contiguous sites of a double helical DNA target forming triple helical structures.

The polynucleotide can be derived from a completely chemical synthesis process, such as a solid phase mediated chemical synthesis, or from a biological origin, such as through isolation from almost any species that can provide DNA or RNA, or from processes that involve the manipulation of nucleic acids by molecular biology tools, such as DNA replication, PCR amplification, reverse transcription, or from a combination of those processes. Modifications to introduce a universal primer of the invention may be performed post-synthetically; or a modified polynucleotide may be used as a primer in a synthetic reaction, e.g. PCR; and the like.

As is used in the art, the term "oligonucleotide" usually refers to shorter molecules, usually of at least about 3 bases in length, more usually at least 4, 5, or 6 bases; for many embodiments of the invention, preferred oligonucleotides are at least 7 bases, at least 8 bases, at least 10 bases, at least 12 bases, and not more than about 100 bases in length, usually not more than about 50 bases in length, or any length range between any two of these lengths. The term "polynucleotide" may refer to any length of nucleic acid greater than a single base; although in many instances will be used to refer to molecules as present in living organisms, which range from about 50 bases in length to many megabases, in the case of genomic DNAs. The linkers described herein may be readily attached to any polynucleotide. For many assays of interest, one probe, which may comprise the cleavable linker or the reducing agent, will be of a length that is sensitive to small differences in sequence.

"Probe set", as used herein, refers to a set of at least two compatible probes that are used to detect a target analyte in a sample. In some embodiments, when a first probe and a second probe are brought into close proximity, e.g. by hybridizing to neighboring sequences on a target polynucleotide, the probes react thereby cleaving one or more α-azidoether moieties and releasing one or more quenchers. In some embodiments, a first probe reacts consecutively with two second probes, where each second probe reacts thereby consecutively releasing two quenchers. The term "proximity" refers to the relative positions of the probes and/or the reacting moieties of the probes, and occurs when the two groups are sufficiently close to trigger a reaction.

In some embodiments, a probe set contains a cleavable probe and a second probe containing a phosphine reducing agent. The second probe comprises a specific binding moiety, e.g., a polynucleotide with a sequence such that it hybridizes adjacent to a cleavable probe on a target sequence; and antibody or fragment thereof, a ligand, minor groove binder, etc., as defined herein. The phosphine reducing agent of the second probe may be attached via a substituent of the phosphine, e.g., via the carboxy substituent of 4-carboxyphenyldiphenylphosphine.

In particular embodiments the second probe is of the structure of formula (XII):

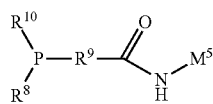
(XII)

where $R^8$, $R^9$ and 10 are independently selected from an alkyl, an aryl and a heterocycle; and $M^5$ is a specific binding moiety. In some embodiments, $M^5$ is a polynucleotide.

In particular embodiments, the second probe is of the structure of formula (XIII):

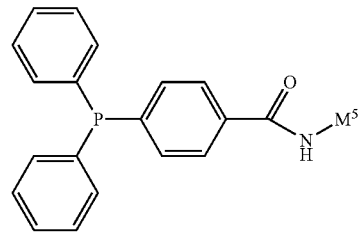
(XIII)

where $M^5$ is as defined above.

In particular embodiments, the second probe is of the structure of formula (XIV):

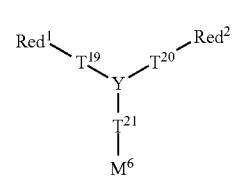
(XIV)

where $Red^1$ and $Red^2$ are phosphine reducing agents;
$T^{19}$, $T^{29}$ and $T^{21}$ are tethers;
Y is carbon or nitrogen; and
$M^6$ is a specific binding moiety.

In particular embodiments, the second probe is of the structure of formula (XV):

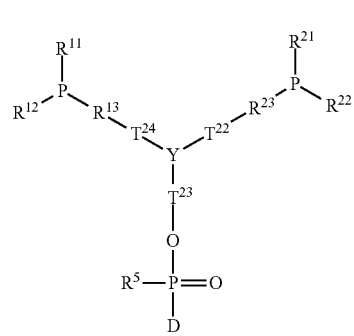
(XV)

where $R^{11}$, $R^{12}$, $R^{13}$, $R^{21}$, $R^{22}$ and $R^{23}$ are independently selected from an alkyl, an aryl, a heterocycle;
$T^{22}$, $T^{23}$ and $T^{24}$ are tethers; and
Y, $R^5$ and D are as defined above in formula (X).

In a particular embodiment, a probe set includes the cleavable probe of the structure of formula (IX) and the second probe of the structure of formula (XIII), that bind to adjacent regions of a target sequence, under conditions sufficient to trigger cleavage of the quencher, e.g., cleavage of a dabsyl moiety from the polynucleotide $M^2$ of the cleavable probe (IX).

In a particular embodiment, a probe set includes the cleavable probe of the structure of formula (X) and the second probe of the structure of formula (XIII), that bind to adjacent regions of a target sequence, under conditions sufficient to trigger cleavage of a quencher, e.g., cleavage of a dabsyl moiety from the polynucleotide of the cleavable probe (X).

DETECTION METHODS

Methods are provided for the detection of analytes utilizing probes of the invention. Such methods include, without limitation, sequence specific detection of nucleic acids in vitro and in vivo. The cellular detection is simple, requiring only a single experimental step. The probes of the invention, which may be referred to as "Q-STAR" (quenched Staudinger triggered α-azidoether release) and "2-STAR" (double quenched Staudinger triggered α-azidoether release) probes utilize a quencher release strategy for fluorescence turn-on. The probes of the invention offer a number of beneficial properties, including low backgrounds, fast reaction kinetics and improved signal amplification relative to conventional probes. The probes of the invention are stable to cellular constituents, including water, reducing background fluorescence in vivo, where stable means background decomposition of the probes is sufficiently low to enable a clear detection signal over background signal. Finally, the quencher-release approach is versatile, where the use of different quencher and fluorophore groups allows the design of probes with a wide spectral range. The performance of the probe of the invention makes them attractive for widespread applications in nucleic acid detection assays.

In some embodiments, methods are provided for the specific detection of single stranded polynucleotides, including mRNA, genomic DNA, extrachromosomal DNA, rRNA, siRNA, miRNA, ncRNA, etc., in a variety of platforms, including live cells. In another embodiment, methods are provided for the specific detection of double stranded polynucleotides. In another embodiment, methods are provided for the specific detection of peptides or proteins. In another embodiment, methods are provided for the specific detection of an analyte through use of an affinity reagent, for example an antibody. Samples suitable for analysis include isolated analytes, for example, isolated polynucleotides, peptides or proteins; cell lysates; whole cells and tissues, which may be live or fixed; and whole organisms. Kits for practice of the methods are also provided.

In such embodiments, a probe of the invention is brought into contact with a sample suspected of containing an analyte of interest, under conditions in which the specific binding moiety of the probe can bind to its cognate analyte. Typically a probe comprises a fluorophore conjugated to the specific binding moiety, which fluorophore is quenched by one or more quenchers linked to the specific binding moiety via one or more α-azidoether moieties. Upon binding, the probe is subject to cleavage triggering conditions, thereby releasing the one or more quenchers and allowing detection of the unquenched fluorophore. In some embodiments the position of the one or more quenchers and the fluorophore are inversed.

In some embodiments of the invention, a method of detecting a target polynucleotide sequence comprises contacting a sample with a set of probes, where the probe set includes a first probe comprising a fluorophore, a quencher, a cleavable α-azidoether moiety, a probe region complementary to a first region of the target polynucleotide sequence conjugated to a fluorophore, as described herein. The probe set further includes a second probe comprising a probe region complementary to a second region of the target polynucleotide sequence, and a moiety capable of cleaving the cleavable linker. When the first and second probes are brought into proximity through hybridization, the quencher is cleaved from the first probe, allowing detection of the unquenched fluorophore. In some embodiments, the second probe comprises a phosphine reducing agent, for example as described herein.

In some embodiments of the invention, a method of detecting a target polynucleotide sequence comprises contacting a sample with a set of probes, where the probe set includes a first probe comprising a fluorophore, two quenchers, two cleavable α-azidoether moieties, and a probe region complementary to a first region of the target polynucleotide sequence conjugated to the fluorophore, as described herein. The probe set further includes a second probe comprising a probe region complementary to a second region of the target polynucleotide sequence, and a moiety capable of cleaving a cleavable α-azidoether moiety. When the first and second probes are brought into proximity through hybridization, one of the quenchers is cleaved from the first probe. Dissociation of the reacted second probe and hybridization of a further molecule of unreacted second probe leads to cleavage of the second quencher, and allows detection of the unquenched fluorophore. A first probe that generates a fluorescent signal only after two quenchers have been cleaved from the probe can reduce the probability of unintended reactions occurring off-template or with mismatched targets, and give low initial background fluorescence. In some embodiments, the second probe comprises a single phosphine reducing agent, for example as described herein, such that two molecules of second probe are needed to cleave both quenchers. In some embodiments, the second probe can include two cleaving moieties (e.g., two phosphine reducing agents), each moiety capable of cleaving one of the cleavable α-azidoether moieties. In this case, the second probe can lead to release of two quenchers after a single hybridization binding event.

The sequence of the probe(s) is selected to be complementary, competitive, mismatched, etc. with respect to a target sequence, as dictated by the specific interests of the method. In some embodiments, the probe sequences are chosen to be sufficiently selective that there is a detectable difference between binding to a perfect match at the target, and to a single nucleotide mismatch at the target. A highly selective probe binds with high preference to the exact complementary sequence on a target strand as compared to a sequence that has one or more mismatched bases. The probes may contain moieties specifically designed to enhance the sequence selectivity. Less selective probes are also of interest for some embodiments, where hybridization is sufficient for detectable reactions to occur in the presence of one, two three or more mismatches, where a mismatch may include substitutions, deletions, additions, etc.

A "target sequence" refers to the particular nucleotide sequence of the target polynucleotide, which may be hybridized by a probe or probes. Exemplary targets include viral polynucleotides, bacterial polynucleotides (such as mRNA, rRNA), and eukaryotic rRNA, mRNA, genomic DNA, miRNA etc. A target sequence can also be an RNA or DNA produced by nucleic acid amplification assays including polymer chain reaction, nested polymer chain reaction and rolling cycle amplification.

As used herein, a "test sample" is a sample suspected of containing nucleic acids to be analyzed for the presence or amount of an analyte polynucleotide. Nucleic acids of the test sample may be of any biological origin, including any tissue or polynucleotide-containing material obtained from a human. For example, the nucleic acids of the test sample may be from a biological sample that may include one or more of: tissue or organ lavage, sputum, peripheral blood, plasma, serum, bone marrow, biopsy tissue including lymph nodes, respiratory tissue or exudates, gastrointestinal tissue, cervical swab samples, semen or other body fluids, tissues or materials. Biological samples may be treated to disrupt tissue or cell structure, thereby releasing intracellular components into a solution which may contain enzymes, buffers, salts, detergents and the like. Alternative sources of nucleic acids may include water or food samples that are to be tested for the presence of a particular analyte polynucleotide that would indicate the presence of a microorganism. In other embodiments, whole cells are provided in a sample, where methods of detection include fluorescence activated cell sorting. In other embodiments biological samples may be obtained from cell cultures or tissue cultures.

Applications for such methods include in vivo and in vitro diagnostics, including clinical diagnostics, research in the fields of molecular biology, high throughput drug screening, veterinary diagnostics, agricultural-genetics testing, environmental testing, food testing, industrial process monitoring, etc. In vitro diagnostics and clinical diagnostics relate to the analysis of nucleic acid samples drawn from the body to detect the existence of a disease or condition, its stage of development and/or severity, and the patient's response to treatment. In high throughput drug screening and development, nucleic acids are used to analyze the response of biological systems upon exposure to libraries of compounds in a high sample number setting to identify drug leads. Veterinary diagnostics and agricultural genetics testing provide a means of quality control for agricultural genetic products and processes. In environmental testing, organisms and their toxins that characterize an environmental medium, e.g. soil, water, air, etc., are analyzed. Food testing includes the qualitative identification and/or quantitation of organisms, e.g. bacteria, fungi, etc., as a means of quality control.

In such assays, a change in fluorescent signal is generated upon the presence of a complementary nucleic acid sequence in the analyte. The fluorescent signal is monitored and quantified with fluorescence detectors, such as fluorescence spectrophotometers, microplate readers, UV lamps, flow cytometry, fluorescence microscopes, fluorescence activated cell sorting, commercial systems that allow the monitoring of fluorescence in real time reactions, or, in some instances, by the human eye.

In one embodiment, a homogeneous assay is conducted. In this embodiment of the invention, the nucleic acid probes hybridize with a complementary nucleic acid sequence, if present in the target, to release the one or more quencher groups and effect a change in fluorescence. With appropriate target standards and concentration versus signal standard curves the method can easily be used to quantitate the target. In addition to single stranded target nucleic acids, double stranded target nucleic acids can also be detected by the nucleic acid probe following denaturation. Double stranded targets can further be detected by the formation of triple helices. Targets that can be specifically detected and/or quantified with this method include, but are not limited to, plasmid DNA, cloning inserts in plasmid DNA, mRNA transcripts, ribosomal RNA, PCR amplicons, restriction fragments, synthetic oligonucleotides, as well as any other nucleic acids and oligonucleotides.

In another embodiment, a plurality of probes is employed in assays to detect or quantify one or more nucleic acid targets, which assays may be performed in solution; in cells; on a solid substrate; etc. Various formats may be used in such assays. The composition of fluorophores and/or quenchers will be selected to provide the desired information, including the use of multiple fluorophores with distinguishable signals.

Competition assays may also be performed. For example, a single probe comprising a phosphine group, and complementary to a sequence of interest may be used with a plurality of probes comprising fluorophores and complementary to potentially variable neighboring sequences, e.g. polymorphic sequences, alternatively spliced sequences, etc. The probe having greatest complementarity can win the competition, yielding a fluorescence signal specific to that probe.

Assays based on detection of sequences present in individual cells may utilize fixed or living cells. Probes can be introduced into live cells using any one of many well-known methods for bringing oligonucleotides into cells, including electroporation, calcium phosphate transfection, ionic shock, microinjection, pore-forming peptides, digitoin permeabilization, uptake reagents, fusion of vesicles, etc. Many such reagents are commercially available. Such methods may utilize carrier molecules, including calcium-phosphate, DEAE dextran and cationic lipids. Nucleic acids can be adsorbed to unilamellar liposome vesicles comprising cationic lipids mixed with neutral lipids, which vesicles may be modified by the inclusion of various commercially available components, e.g. FuGENE 6; X-tremeGENE Q2; etc. (Roche Applied Science). Cationic polymers, including dendrimeric polyamines or homopolymers of positively charged amino acids such as poly-L-lysines, poly-D-lysines and poly-L-ornithines, HIV tat, *Pseudomonas exotoxin, Drosophila* Antennapedia and HSV-1 VP22 protein may also be used as carriers. Agents that enhance uptake may be covalently conjugated to the probes. Examples include cationic peptides, cholesterol, arginine-rich peptides, etc. Pore-forming peptides include Streptolysin O. For bacterial cells probe delivery may be assisted by surfactants, e.g., sodium dodecyl sulfate.

Flow cytometry is a convenient method to quantitate fluorescence signals from cells. Flow cytometry methods are known in the art, and described in the following: Flow Cytometry and Cell Storing (Springer Lab Manual), Radbruch, Ed., Springer Verlag, 2000; Ormerod, Flow Cytometry, Springer Verlag, 1999; Flow Cytometry Protocols (Methods in Molecular Biology, No 91), Jaroszeski and Heller, Eds., Humana Press, 1998; Current Protocols in Cytometry, Robinson et al., eds, John Wiley & Sons, New York, N.Y., 2000. The readouts of selected fluorophores are capable of being read simultaneously, or in sequence during a single analysis, allowing of up to 5 or more fluorescent colors simultaneously. Readouts from such assays may be the mean fluorescence associated with individual fluorescent molecules, or the average fluorescence intensity, the median fluorescence intensity, the variance in fluorescence intensity, or some relationship among these.

Microscopic analysis of single cell multiparameter and multicell multiparameter multiplex assays are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

In a particular embodiment of the invention, RNA molecules from a biological source are detected and/or quantified. The RNA may be directly obtained from cells of interest; may be present in living or fixed cells; or may be converted to cDNA molecules and/or further amplified by PCR.

Such assays may be conducted with rRNA or mRNA samples obtained from a biological system under different environmental conditions, such as exposures to varying concentration of a drug candidate or mixtures of drug candidates, which can provide data on the efficacy, the safety profile, the mechanism of action and other properties of the drug candidates that are required in drug development. Alternatively, tissue samples may be probed for the presence of clinical conditions, e.g., the presence of pathogens; expression of tumor associated sequences; and the like.

In another embodiment of the invention, the probes are used to detect or quantify nucleic acid targets from genomic DNA, in order to analyze for the presence or absence of polymorphisms in the genomic DNA. The polymorphisms can be deletions, insertions, or base substitutions or other polymorphisms of the genomic DNA. Typically the polymorphisms are single nucleotide polymorphisms (SNPs), gene rearrangements, allelic variants; and the like.

In another embodiment of the invention, the probes are used in detection assays, such as, detection of single nucleotide polymorphisms in real time PCR applications, genetic discrimination of pathogens, analysis of pathological tissue samples, fluorescence activated cell sorting based on genetic variations, and genetic identification of specific alleles in vivo,

SYNTHETIC METHODS

The linkers of the invention are useful in the biosynthesis of compounds having a cleavable linker activated by mild reducing agents. A specific binding moiety suitable for use in a probe of the invention may be conjugated to one or more cleavable linkers of the invention via one or more suitable tethers or functional groups. In some cases, bioconjugation strategies and functional groups for use with/in cleavable linkers of the present invention, are described in Hermanson, "Bioconjugate Techniques," Academic Press, 2nd edition, Apr. 1, 2008. In some cases, protecting groups and functional groups for use with/in cleavable linkers of the present invention are described in Greene Protecting Groups in Organic Chemistry, Wuts and Greene, Wiley-Interscience, 4th edition, Oct. 30, 2006. For example, a synthetic polynucleotide may be synthesized with a modified terminal polynucleotide residue that contains a tether, e.g., an amino tether, suitable for conjugating to a cleavable linker, e.g., the carboxylic acid group of a cleavable linker using a EDC/NHS procedure as described by Hermanson.

KITS

Kits are provided for practicing the subject methods. The kits according to the present invention may comprise at least: (a) a probe set as described herein; and (b) instructions for using the provided probe set. Such probe sets may be provided lyophilized, in solution, or bound to a substrate.

Kits may also be provided for use in the synthesis of probes, etc., comprising a linker of the invention; which is optionally loaded with a functional group; which may be provided with reagents for reacting with a polynucleotide or other suitable biomolecule.

The subject kits may further comprise additional reagents which are required for or convenient and/or desirable to include in the reaction mixture prepared during the subject methods, where such reagents include reagents and buffers for DNA synthesis; columns; and the like.

The various reagent components of the kits may be present in separate containers, or may all be precombined into a reagent mixture for combination with samples. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXPERIMENTAL

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Described herein are probes for templated fluorescence activation for the detection of polynucleotides. The described quenched Staudinger triggered α-azidoether release (Q-STAR and 2-STAR) probes are fluorophore-containing oligonucleotide probes, whose fluorescence is deactivated by one or more quenchers attached via an α-azidoether cleavable linker. Reduction of the azide functionalities, for example by triphenylphosphine (TPP) groups, triggers the cleavage of the cleavable linkers and the release of the one or more quenchers, eliciting a robust fluorescence turn-on signal.

Example 1

FIG. 1 illustrates the detection of nucleic acids by templated fluorescence activation of Q-STAR probes. For example, a Q-STAR probe and a TPP-modified DNA bind to a common target strand. Proximity-induced reduction of Q-STAR's azide functionality results in cleavage of the α-azidoether linker and release of the quencher, yielding a fluorescence signal. Subsequent probe exchange allows for multiple turnovers, isothermally amplifying the signal.

To prepare Q-STAR probes, the α-azidoether linker 1 was designed and synthesized (see Scheme 1 for details), which contains an amino functionality suitable for chemical derivatization. Modification of 1 with dabsyl quencher and hydrolysis of the ester provided 2 (Scheme 2) as a phosphine-responsive quencher release linker (i.e. a cleavable linker) which is amenable to bioconjugation. Attachment of 2 to DNA (yielding 3) proceeded readily using solid-phase amide coupling to 5'-amino-modified DNA. Triarylphosphine-DNA conjugates (TPP-DNA) were prepared as previously described (Franzini, R. M.; Kool, E. T. ChemBioChem 2008, 9, 2981-2988). using 3'-amino-modified DNA synthesized in the 5'→3' direction.

Scheme 1. Synthesis of the α-azidoether linker (1).
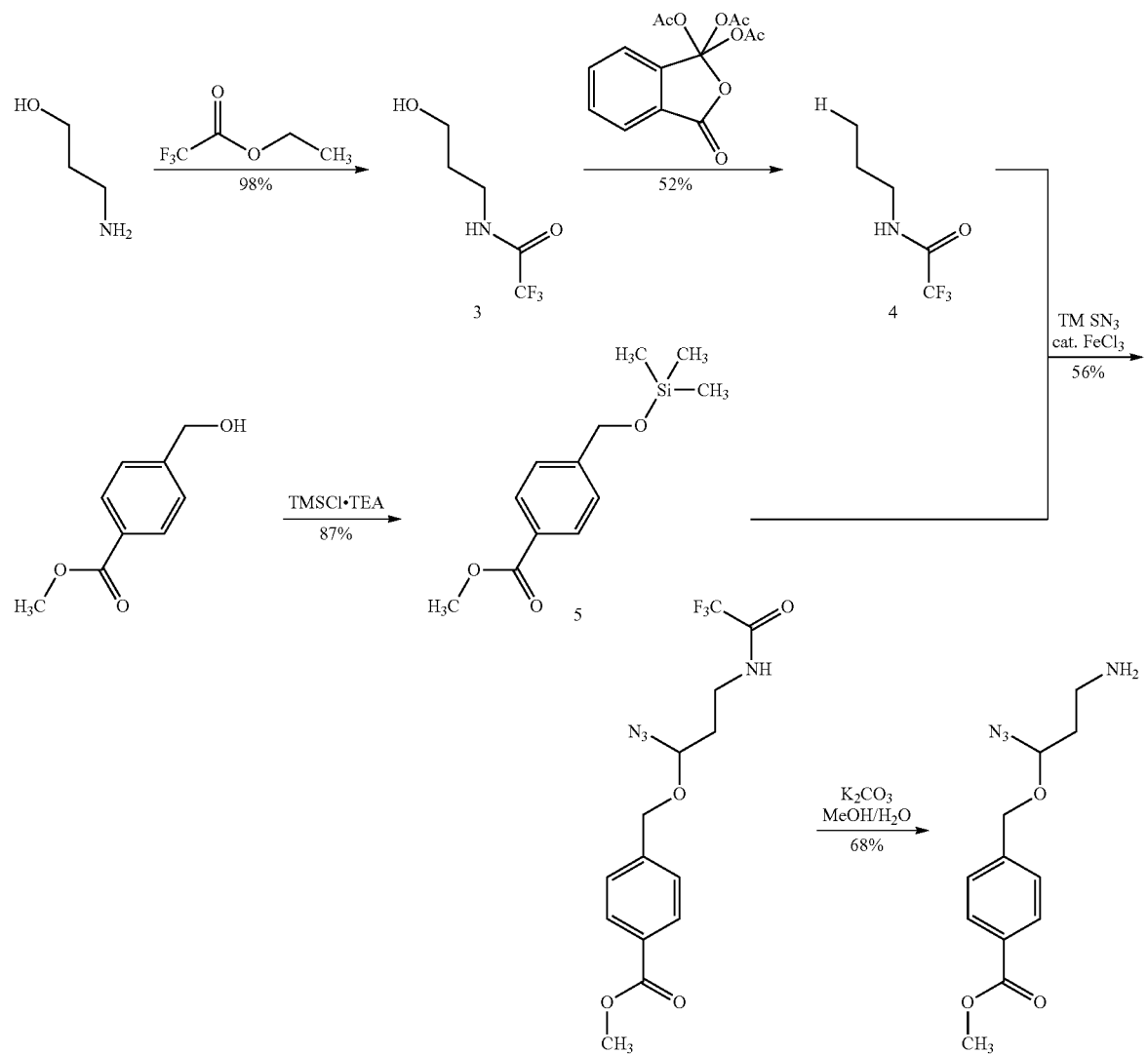
Scheme 2
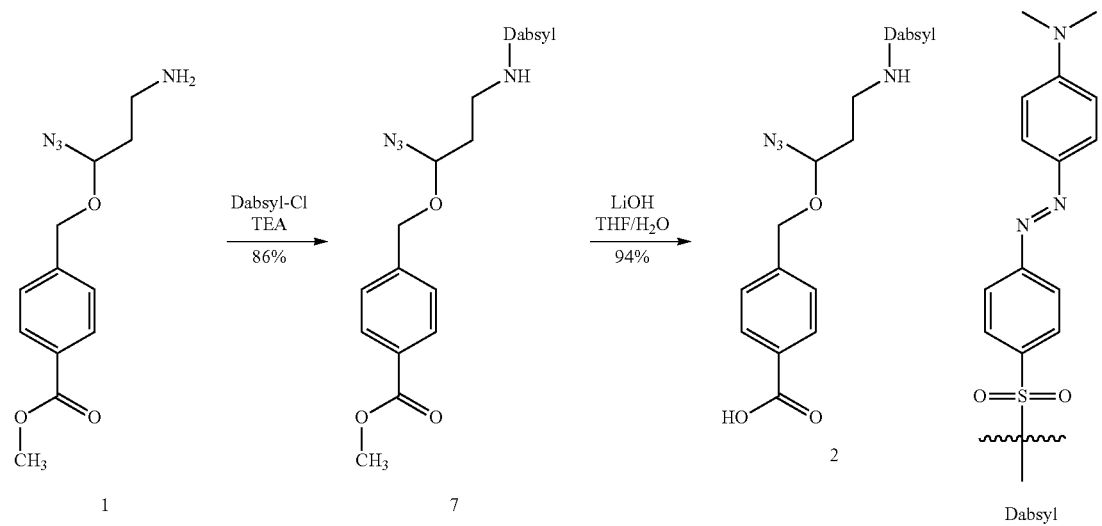

A second cleavable linker (13) was prepared, which contains an alternative linker structure and is labeled with a black hole quencher 2 (BHQ2) (see Scheme 3 for detail). The linker can be conjugated to amine containing binding moieties e.g. amino-modified DNAs by peptide bond formation.

Scheme 3: Synthesis of quencher containing linker 13.

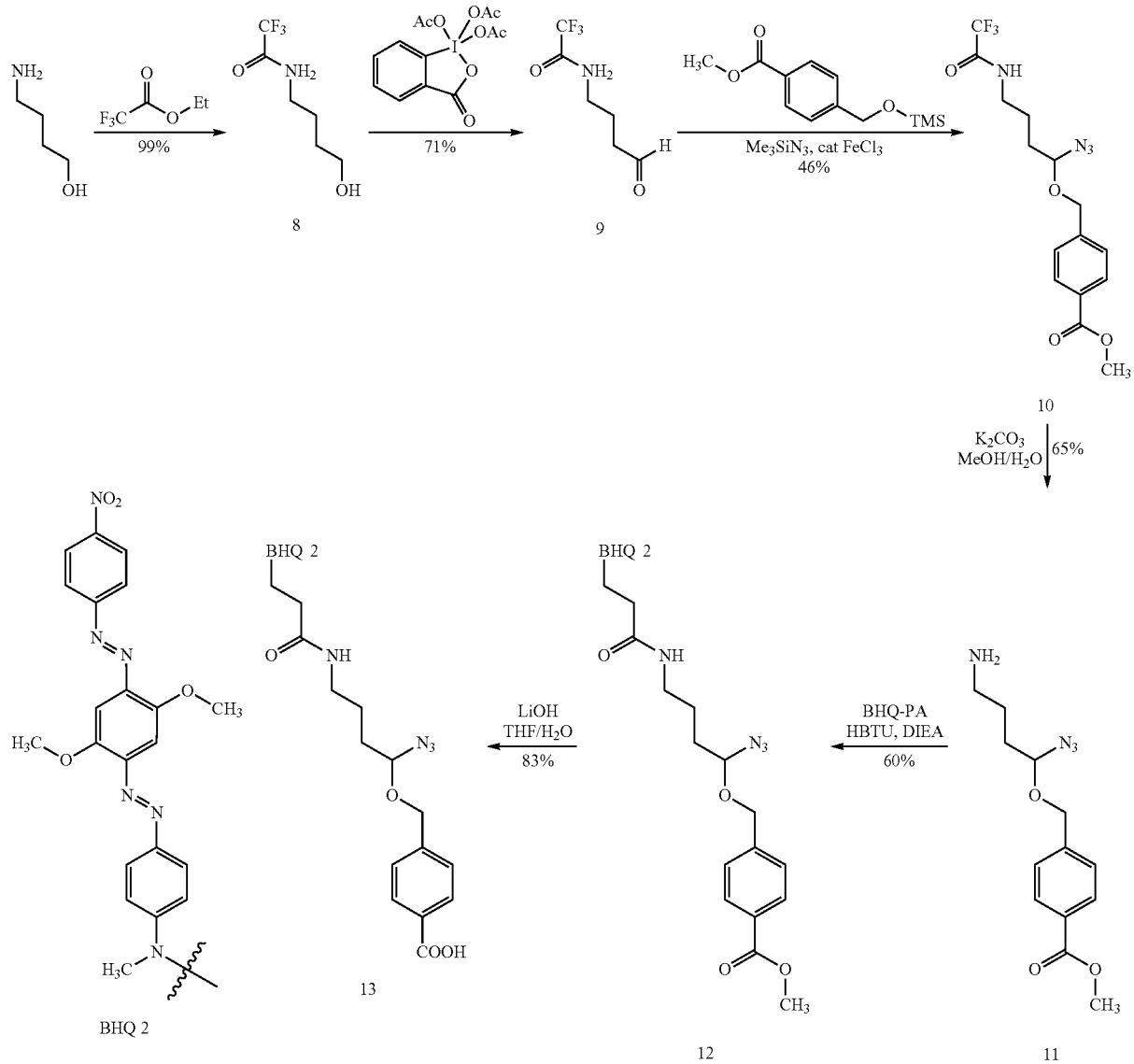

To assess the performance of Q-STAR probes in a template-dependent configuration, a fluorescein-labeled probe was prepared (green STAR) (FIG. 2a) complementary to a sequence element of *Escherichia coli* 16S rRNA. (Silverman, A. P.; Kool, E. T. Nucleic Acids Res. 2005, 33, 4978-4986). To trigger the release of its quencher, a TPP-DNA conjugate was prepared, designed to bind directly adjacent to green STAR on the 16S RNA target sequence. For solution studies, a target synthetic DNA (EC DNA) homologous to the 16S RNA sequence was used.

Upon addition of TPP-DNA (600 nM) to a solution containing green STAR (200 nM) and EC DNA (200 nM) a strong fluorescence signal emerged (FIG. 2b). Fluorescence activation at 37° C. was rapid, reaching 90% conversion within 32 min, and substantial, with a 61-fold fluorescence increase after 115 min. A single mismatch in the target strand reduced the rate of reaction dramatically as illustrated for SE DNA template (FIG. 2b). The relative kinetic mismatch discrimination, estimated from the initial rate of reaction, between these closely related sequences was 120±20. Omitting either the EC DNA template or TPP-DNA further reduced the rate of reaction, suggesting insignificant background signal and establishing substantial rate acceleration induced by the matched template.

In a templated detection scheme, each DNA/RNA analyte can, in principle, mediate multiple reactions and provide an amplified fluorescence signal, unless long probe sequences or bond formation hinders product dissociation (Abe, H.; Kool, E. T. J. Am. Chem. Soc. 2004, 126, 13980-13986; Grossmann, T. N.; Strohbach, A.; Seitz, O. ChemBioChem 2008, 9, 2185-2192). To evaluate signal amplification of Q-STAR probes, the template-mediated activation of green STAR was investigated in the presence of substoichiometric amounts of EC DNA (FIG. 2c). The fluorescence intensity of green STAR increased rapidly and significantly exceeded the emission expected for stoichiometric conversion. For example, the fluorescence emission of a sample containing only 2 nM of EC DNA, which corresponds to 1% of the green STAR probe, approached the level of complete fluorescence activation within few hours. This outcome demonstrates that template turnover is efficient for Q-STAR probes, providing a robustly amplified signal under isothermal conditions.

Figure 2:
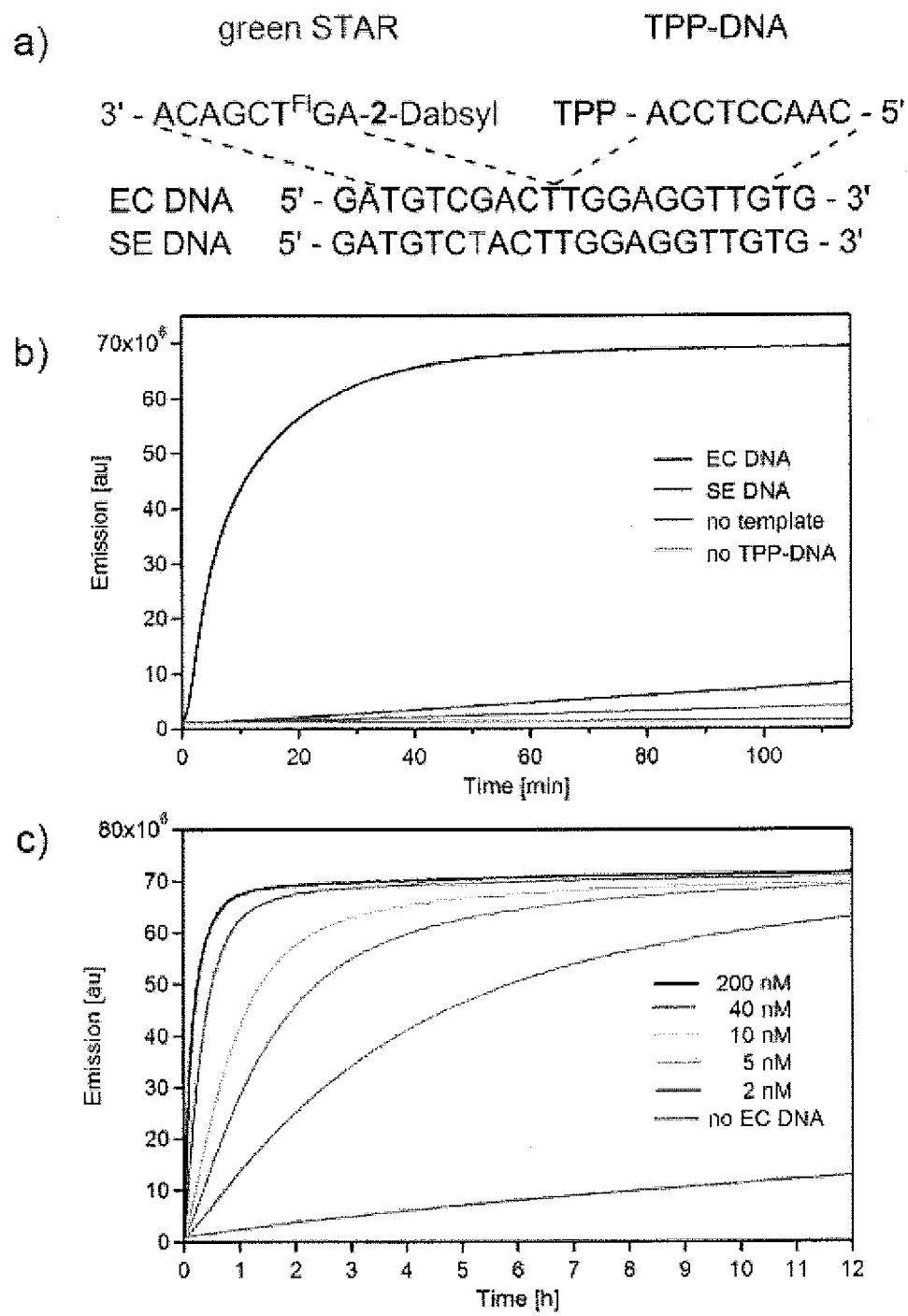
FIG. 2(a)-(c). Template dependence of Q-STAR activation for the detection of complementary EC DNA. a) Sequences of DNA-probes and targets ($T^{Fl}$=Fluorescein labeled dT) b) Time courses of fluorescence activation with varied targets. c) Amplified fluorescence signal in the presence of substoichiometric amounts of EC DNA.

FIG. 2 illustrates the template dependence of Q-STAR activation for the detection of complementary EC DNA. FIG. 2a shows the sequences of DNA-probes and targets (TFI=fluorescein labeled dT). FIG. 2b shows the time courses of fluorescence activation with varied targets. FIG. 2c shows the amplified fluorescence signal observed in the presence of substoichiometric amounts of EC DNA (Conditions: 200 nM green STAR, 200 nM EC DNA or SE DNA, 600 nM TPP-DNA, pH 7.4 tris-borate buffer (70 mM) containing 10 mM $MgCl_2$, 37° C.; λex=494 nm. λem=520 nm).

The potential of the designed Q-STAR probes to discriminate between two bacterial species, *Escherichia coli* and *Salmonella enterica*, was assessed. A polymorphic sequence-element on the 16S rRNA was chosen, that is accessible to hybridization and contains a single nucleotide difference between *E. coli* and *S. enterica* (Silverman, A. P.; Kool, E. T. Nucleic Acids Res. 2005, 33, 4978-4986). A two-color system for distinguishing these microorganisms was designed: the probe complementary to the *E. coli* target (green STAR) contained an internal fluorescein label while the *S. enterica* complementary probe (red STAR) contained both a fluorescein label and a terminal TAMRA fluorophore (Table 1). The latter probe was designed to yield a red signal upon loss of quencher, as a result of Förster resonance energy transfer (FRET) from the fluorescein donor to the TAMRA acceptor (Silverman, A. P.; Baron, E. J.; Kool, E. T. ChemBioChem 2006, 7, 1890-1894). This FRET design allows the green and red signals to be observed simultaneously using a single excitation and a long-pass emission filter.

Green STAR was combined with IR STAR in an alternative two-color probe set to distinguish *E. Coli* and *S. enterica*. IR STAR contains an internal cyanine fluorescent dye (Quasar 670) and the phosphine-cleavable linker 13 containing black hole quencher 2 with a sequence complementary to the 16S rRNA from *S. enterica* (Table 1).

TABLE 1

Sequences of DNA probes

| DNA probes | Sequences |
|---|---|
| green STAR | 5'-Dabsyl-2-AGT$^{FI}$ CGA CA-3' (SEQ ID NO: 1) |
| red STAR | 5'-Dabsyl-2- AGT$^{FI}$ AGA CA-TAMRA-3' (SEQ ID NO: 2) |
| IR STAR | 5'-BHQ2-2-AGT$^{Q670}$ AGA CA-3' (SEQ ID NO: 3) |
| TPP-DNA* | 5'-AGG GCA CAA CCT CCA-TPP-3' (SEQ ID NO: 4) |

TABLE 1-continued

Sequences of DNA probes

| DNA probes | Sequences |
|---|---|
| Helper 1 | 5'-TCG TTT ACG GCG TGG ACT-3' (SEQ ID NO: 5) |
| Helper 2 | 5'-GCT CCG GAA GCC ACG CCT-3' (SEQ ID NO: 6) |

(Silverman, A. P; Kool, E. T. Nucleic Acids Res. 2005, 33, 4978-4986)

Figure 3:
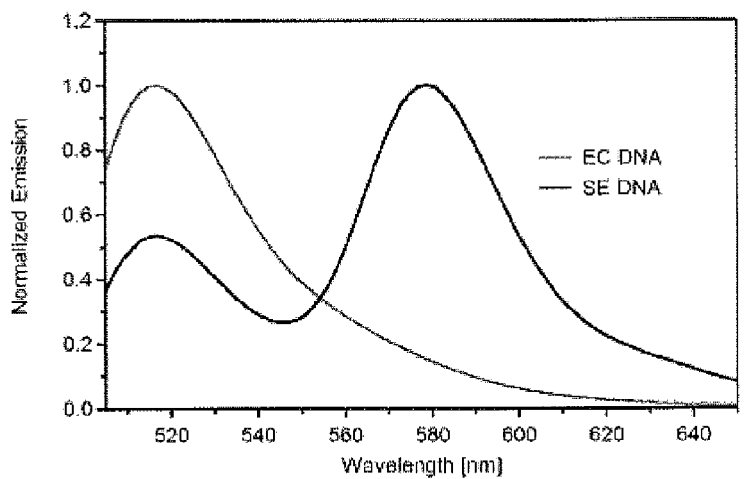
FIG. 3. Normalized fluorescence emission spectra of a mixture of green STAR and red STAR probes incubated with TPP-DNA in the presence of either EC DNA or SE DNA.
Figure 5:
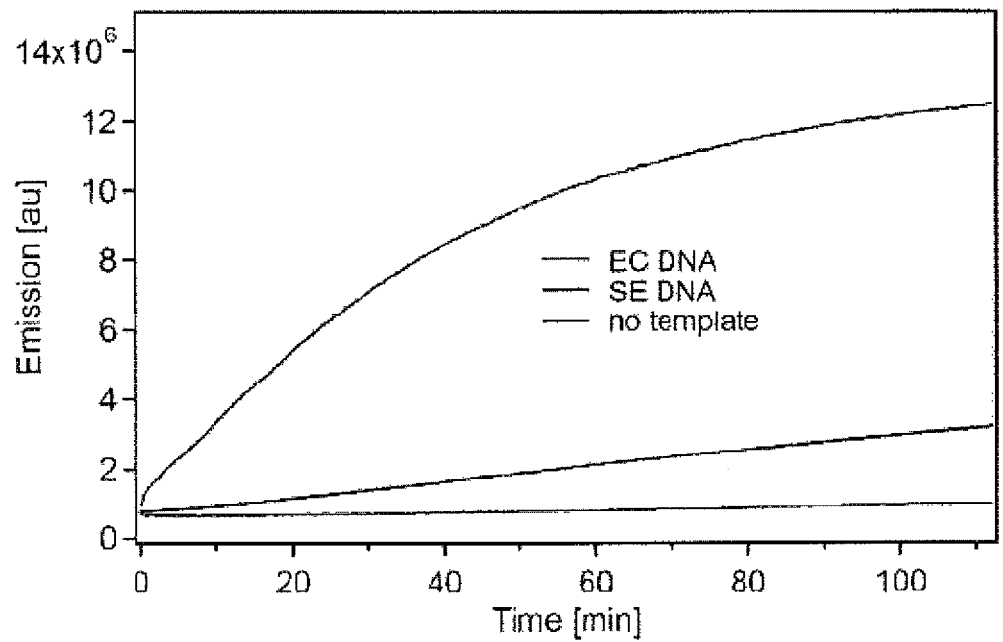
FIG. 5. Reaction kinetics and mismatch discrimination of templated fluorescence activation of red STAR by TPP-DNA.

In an in vitro experiment, the green STAR probe was selectively activated by EC DNA with an emission maximum at $λ_{em}$=517 nm, whereas the red STAR probe was responsive to the SE DNA target and a distinct emission maximum $λ_{em}$=580 nm (FIG. 5). A mixture of green STAR and red STAR probes yielded distinct emission spectra after incubation in the presence of TPP-DNA depending on which target sequence was present (FIG. 3).

Figure 4:
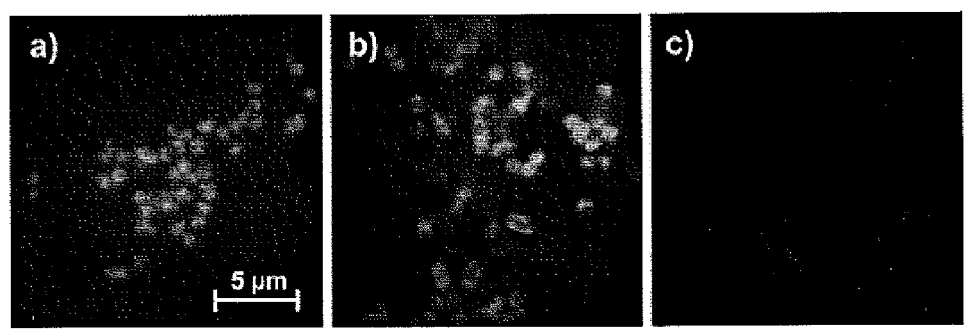
FIG. 4(a)-(c). Two-color discrimination of bacterial species based on 16S rRNA using green STAR and red STAR probes. a) E. coli cells; b) E. coli and S. enterica cells c) S. enterica cells.

To test the probes in vivo, *E. coli* or *S. enterica* cells were incubated with a combination of green STAR and red STAR probes (both 200 nM) and TPP-DNA* (2 μM) at 37° C. in hybridization buffer containing 0.05% SDS to aid probe delivery. Two unmodified helper DNAs (3 μM each) were added to improve target accessibility (see Table 1). Note that no cell fixation steps nor any post-hybridization washes were used. Within 4 h, strong fluorescein (green) emission emerged in the *E. coli* cells (FIG. 4a) whereas *S. enterica* exhibited a distinct red fluorescence (FIG. 4c). Moreover, it was possible to assign single bacteria to either species when the two bacterial types were mixed (FIG. 4b). Thus, the data confirm that Q-STAR probes allow the discrimination of these two microorganisms by a single nucleotide difference. Furthermore, fluorescence activation was negligible without TPP-DNA, suggesting that Q-STAR probes are stable to cellular constituents, in particular to reduction by thiols.

FIG. 5 illustrates Reaction kinetics and mismatch discrimination of templated fluorescence activation of red STAR by TPP-DNA. Conditions: $λ_{ex}$=494 nm, $λ_{em}$=580 nM; c(red STAR)=200 nM, c(TPPDNA)=600 nM, c(template)=200 nM; c($MgCl_2$)=10 mM, c(tris-borate)=70 mM, pH 7.55; T=37° C.

Figure 6:
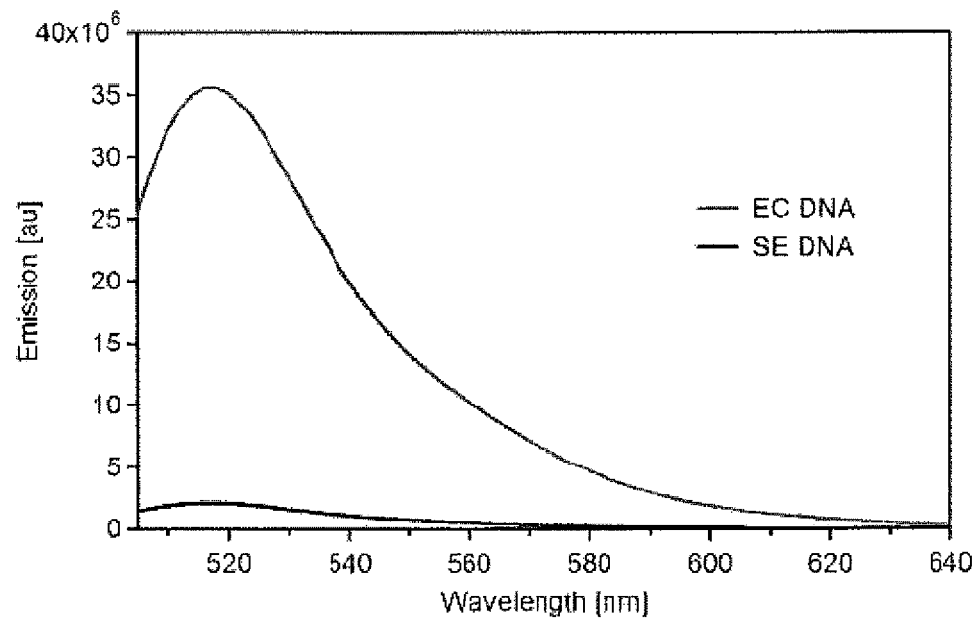
FIG. 6. Fluorescence emission spectrum of green STAR upon reaction with TPP-DNA in the presence of EC DNA and SE DNA.
Figure 7:
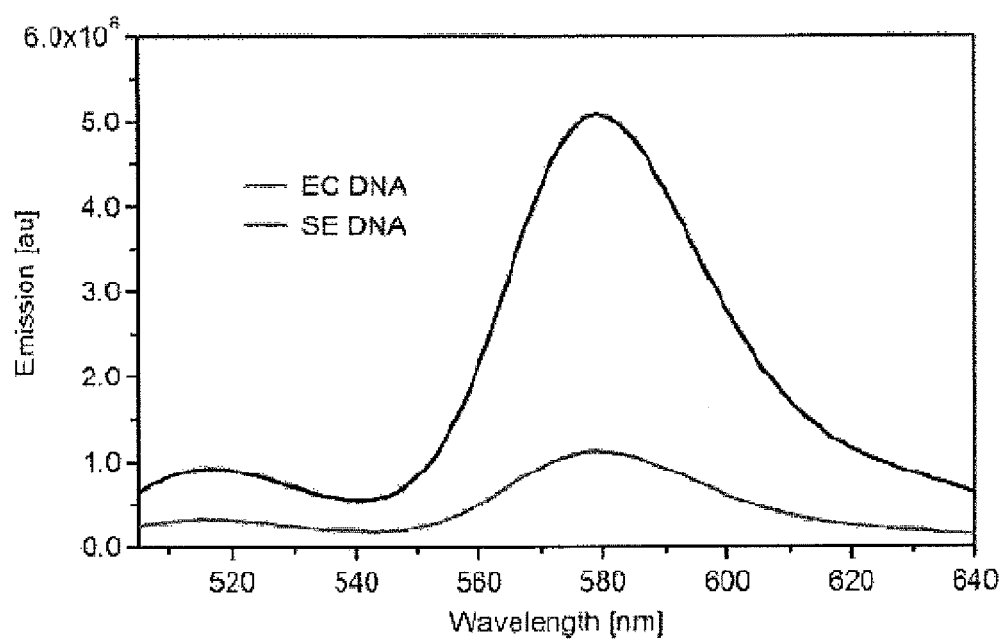
FIG. 7. Fluorescence emission spectrum of red STAR upon reaction with TPP-DNA in the presence of EC DNA and SE DNA.

FIGS. 6 and 7 illustrate the fluorescence emission spectrum of green STAR or red STAR upon reaction with TPP-DNA in the presence of EC DNA and SE DNA, respectively [Conditions: λex=494 nm. c(green STAR)= 200 nM, c(TPP-DNA)=600 nM, c(template)=200 nM; c($MgCl_2$)=10 mM, c(tris-borate)=70 mM, pH 7.55; T=37° C., incubation for 1 h].

Figure 8:
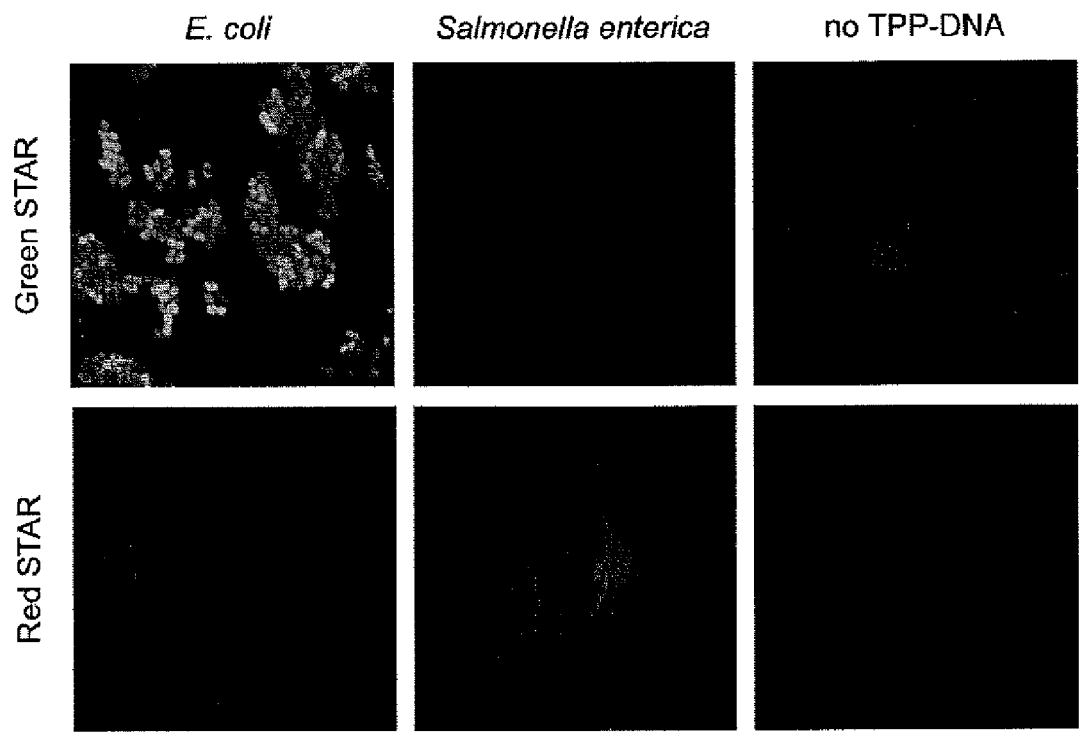
FIG. 8. Selectivity and background fluorescence of Q-STAR probe activation in bacterial cells.

FIG. 8 illustrates the selectivity and background fluorescence of Q-STAR probe activation in bacterial cells [Conditions: c(Q-STAR)=200 nM, c(TPP-DNA)=600 nM, c(helper DNAs)=3 μM. Incubation for 4 h at 37° C.; a B-2A filter set (λex=450-490 nm; dichroic mirror at 500 nm; λem=515 nm) was used for imaging with t=0.5 s exposure for green STAR probes and t=1.0 s exposure for red STAR probes. Images are taken with black/white camera and false colored (green for green STAR probes and red for red STAR probes)].

Figure 9:
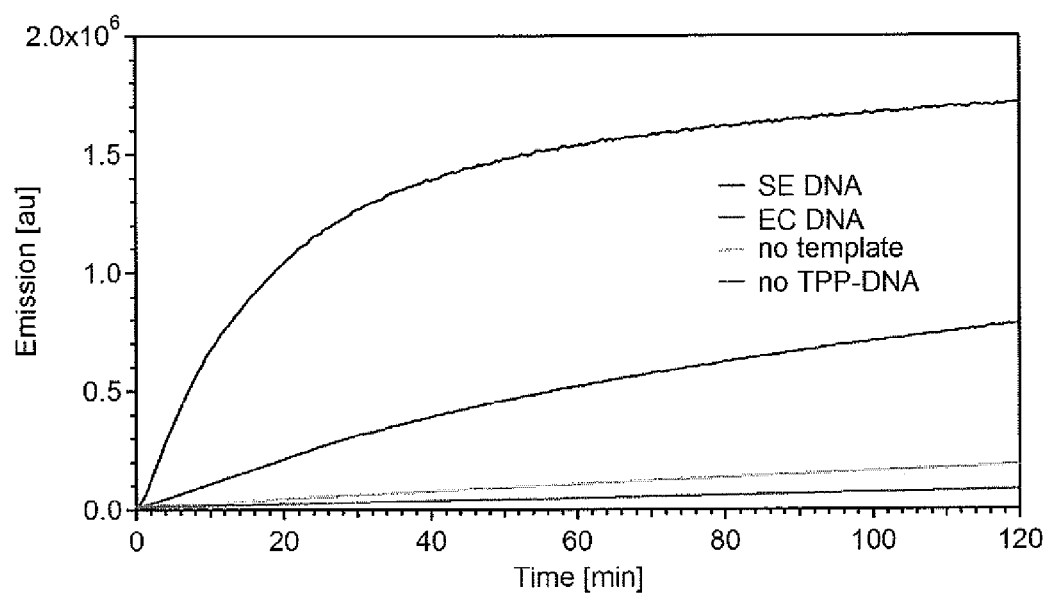
FIG. 9. Reaction kinetics and mismatch discrimination of templated fluorescence activation of IR STAR by TPP-DNA.
Figure 10:
FIG. 10. Two-color discrimination of bacterial species based on 16S rRNA using green STAR and IR STAR probes. a) *E. coli* cells; b) *E. coli* and *S. enterica* cells c) *S. enterica* cells.

IR STAR is sequence selectively activated in the presence of SE DNA (FIG. 9). A pair of green STAR and IR STAR can distinguish *E. coli* and *S. enterica* by fluorescence color (FIG. 10). IR STAR is superior to red STAR because it has a red-shifted emission maximum, reduced spectral overlap with green STAR, and higher fluorescence brightness.

Figure 11:
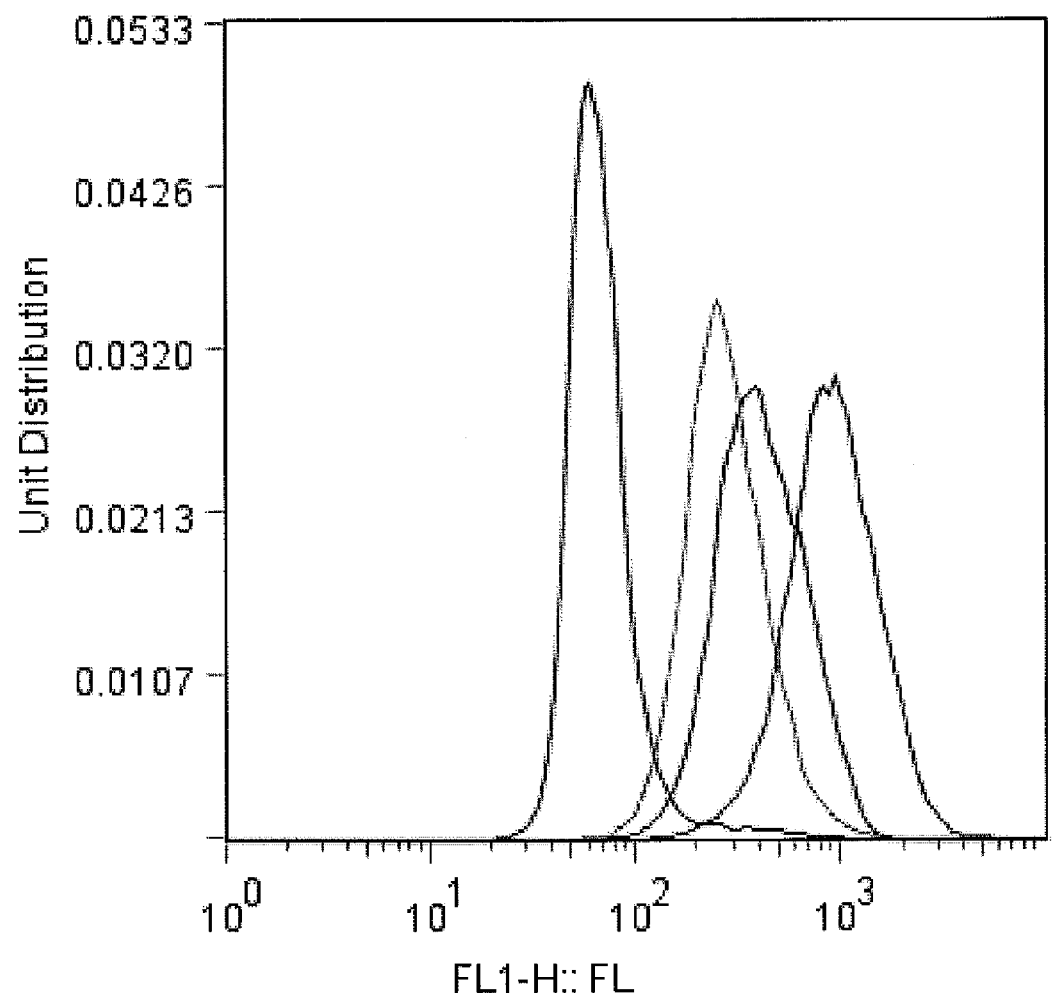
FIG. 11. Flow cytometric analysis of sequence specific detection of 28S rRNA in human cells.

Q-STAR probes provide for the detection of specific RNAs in mammalian cells. A Q-STAR probe specific to a target sequence of the human 28S rRNA (Abe H.; Kool E. T. Proc. Natl. Acad. Sci. 2006, 103, 262-268) was prepared and the corresponding TPP-DNA (Table 1). The Q-STAR probe contained an internal fluorescein fluorophore and the phosphine-cleavable quencher release linker 2. HL-60 cells were permeabilized with Streptolysin O for the delivery of the probes and incubated for 1 h at 4° C. The cells were analyzed by flow cytometry; cells with the correct sequences had a significantly higher fluorescence signal than control cells that contained a scrambled TPP-DNA probe or no TPP-DNA (FIG. 11).

Example 2

2-STAR probes are fluorescein-labeled DNA oligonucleotides containing two 5'-terminal α-azidoether linkers, each carrying a dabsyl quencher, compared to Q-star probes that contain a single linker and quencher. In the 2-STAR reaction design, two successive TPP-mediated reductions are required for fluorescence turn-on (see FIG. 12) rather than one.

Figure 12:
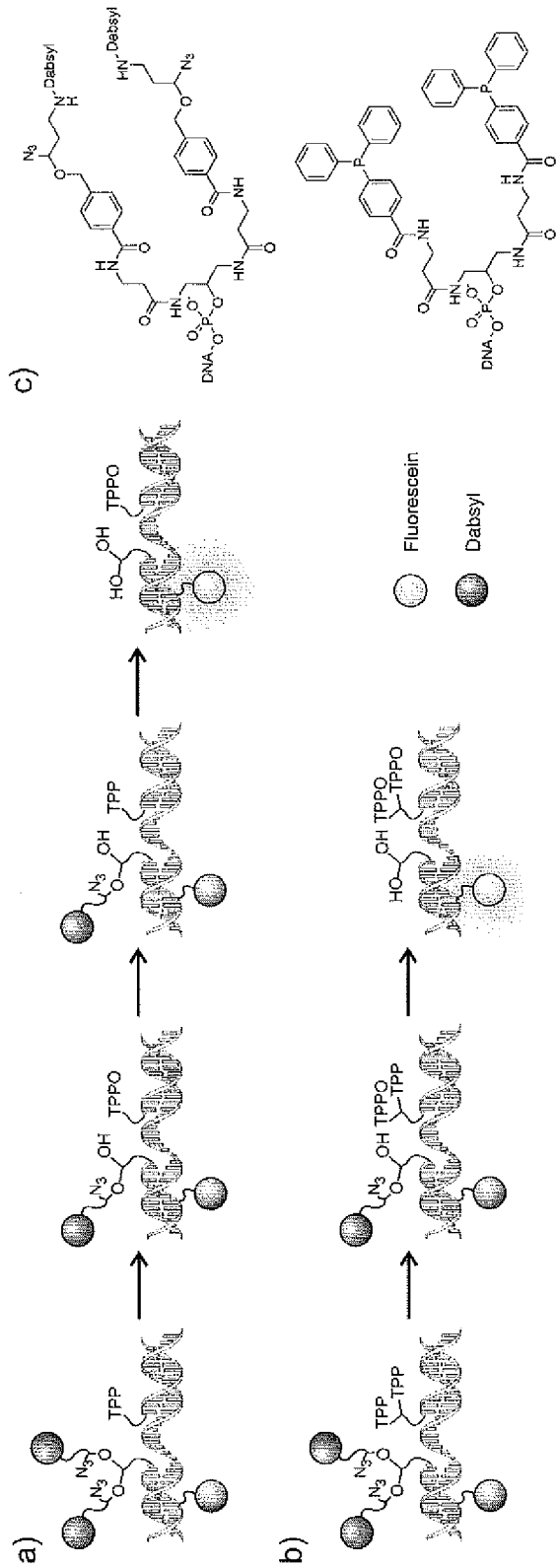
FIG. 12. Template-mediated fluorescence activation scheme based on probes containing two releasable quenchers (2-STAR probes): a) with a single triphenylphosphine TPP-DNA probe; b) with a dual TPP-DNA probe; c) 2-STAR probe (top) and dual-TPP probe (bottom).

FIG. 12 illustrates a template-mediated fluorescence activation scheme based on probes containing two releasable quenchers (FIG. 12c top: 2-STAR probes): a) template-mediated reaction scheme using a DNA probe with a single triphenylphosphine (TPP) moiety where the exchange of two reacting TPP-DNA probes provides for the consecutive release of both quenchers; and b) templated reaction scheme using a DNA probe displaying two TPP-moieties (FIG. 12c bottom), which cleaves both linkers in one binding event.

2-STAR probes were prepared by post-synthetic solid-phase conjugation of two dabsyl-modified α-azidoether linkers to fluorescein-labeled DNAs with two terminal amine functionalities, using methods as described for the preparation of single-linker Q-STAR probes. A 5'-bis-amino-modifier provides for the attachment of two quencher release linkers to the DNA-probe, for example, the monomethoxytrityl (MMt) protected 5'-bis-amino-modifier 15, which was introduced as the terminal phosphoramidite during DNA solid-phase synthesis and deprotected on solid-support by repeated washes with 2% trichloroacetic acid in DCM. Compound 15 was conveniently prepared in two steps and 73% overall yield by coupling two molecules of N-MMt-3-aminopropionic acid (Berube, G.; Richardson, V. J.; Ford, C. H. J. Synth. Commun. 1991, 21, 931-944) to 1,3-diamino-2-propanol followed by the formation of the phosphoramidite (Scheme 4).

The same 5'-bis-amino-modifier was also used for the preparation of the dual-TPP-DNA probes by post-synthetic conjugation of 4-(diphenylphosphino)benzoic acid to modified-DNA synthesized in the 5'→3' direction. Probes that contained a single releasable quencher (Q-STAR probes, prepared for comparison to the new design) or a single TPP moiety (TPP-DNA) were synthesized as previously described.[36] Probes were purified by semi-preparative reverse-phase HPLC and analyzed by MALDI-TOF mass spectrometry (see Supporting Information).

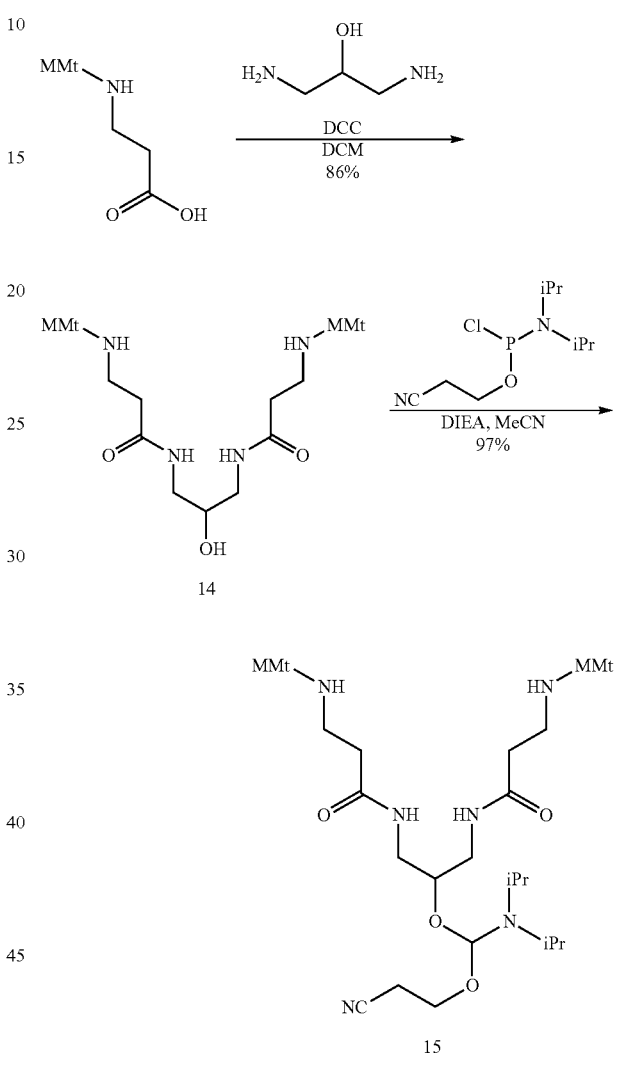

Scheme 4. Synthesis of MMt-protected 5'-bis-amino-modifer phosphoramidite.

To evaluate the performance of 2-STAR probes in a DNA-templated scheme, 2-STAR and TPP-DNA probes were prepared complementary to a sequence element in 16S rRNA that contains a single nucleotide difference between *Escherichia coli* and *Salmonella enterica* (Table 2) (Silverman, A. P.; Kool, E. T. Nucleic Acids Res. 2005, 33, 4978-4986). The TPP-DNA probes were designed to bind adjacent to the 2-STAR probe on the same target site. Two types of TPP-DNAs were prepared, containing either one or two 3'-terminal TPP groups. Both short and long versions of TPP probes were prepared: the shorter probes (DNA 9-mers) were designed to rapidly bind to and dissociate from the target under the reaction conditions, whereas the longer TPP probes (DNA 15-mers) were designed to bind tightly to the target and dissociate slowly under the same conditions. The following nomenclature is used: mono-TPP short probes (ms); dual-TPP short probes (ds); mono-TPP long probes (ml); dual-TPP long probes (dl).

TABLE 2

Sequences of probes and templates.

| Probe | Sequence[a] |
|---|---|
| 2-STAR EC | 5'-(DabAzL)$_2$-AGT$^{FI}$CGACA-3' (SEQ ID NO: 7) |
| 2-STAR SE | 5'-(DabAzL)$_2$-AGT$^{FI}$AGACA-3' (SEQ ID NO: 8) |
| Q-STAR SE | 5'-DabAzI-AGT$^{FI}$AGACA-3' (SEQ ID NO: 9) |
| ms TPP-DNA | 5'-CAACCTCCA-TPP-3' (SEQ ID NO: 10) |
| ml TPP-DNA | 5'-AGGGCACAACCTCCA-TPP-3' (SEQ ID NO: 4) |
| ds TPP-DNA | 5'-CAACCTCCA-(TPP)$_2$ (SEQ ID NO: 11) |
| dl TPP-DNA | 5'-AGGGCACAACCTCCA-(TPP)$_2$-3' (SEQ ID NO: 12) |
| EC-DNA | 5'-GATGTCGACTTGGAGGTTGTGCCCTTG-3' (SEQ ID NO: 13) |
| SE-DNA | 5'-GATGTCTACTTGGAGGTTGTGCCCTTG-3' (SEQ ID NO: 14) |

[a]TFI = 5'-fluorescein labeled deoxythymidine;
DabAzL = Dabsyl containing α-azidoether linker;
TPP = triphenylphosphine;
EC = *E. coli*;
SE = *Salmonella enterica*.

Figure 13:
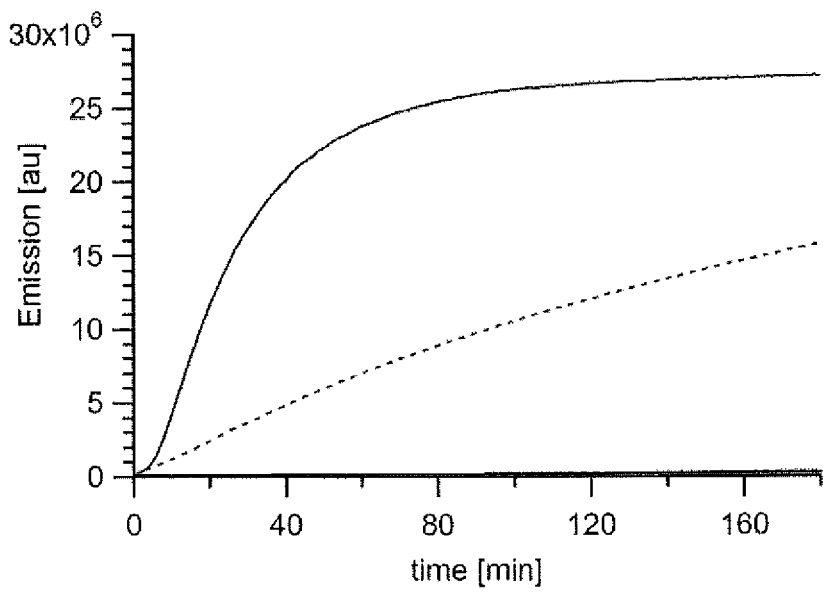
FIG. 13. Kinetic analysis of template-mediated fluorescence activation of 2-STAR EC by DNA probes with a single triphenylphosphine (TPP) modification and different sequence lengths: ms TPP-DNA (solid lines) and ml TPP-DNA (dashed lines) (matched template EC-DNA, red traces; mismatched template SE-DNA, blue traces; no template, green traces).

Fluorescence activation of 2-STAR probes with mono TPP-DNAs. Initial experiments compared the reactivity of the dual-quencher (2-STAR) probes compared to the single-quencher probes. The 2-STAR probe (sequence EC, 100 nM) was co-incubated with the 9-mer (ms) TPP-DNA (600 nM) in the presence of the complementary template EC-DNA (100 nM). Fluorescence monitoring revealed that the template efficiently induced the reaction between 2-STAR EC and ms TPP-DNA, generating a strong increase in fluorescein emission ($\lambda_{ex}$=494 nm; $\lambda_{em}$=521 nm) (FIG. 13). The appearance of fluorescence was delayed for several minutes when compared to single-quencher Q-STAR probes of the same sequence and the rate was moderately reduced. These kinetic differences are consistent with the requirement for two consecutive quencher release events to occur, with the initial delay phase corresponding to buildup of non-fluorescent mono-dabsyl intermediates. Despite this delay, the overall rate of 2-STAR activation remained rapid and the conversion approached 90% in less than 90 minutes.

The fluorescence turn-on value (emission after complete conversion divided by emission prior to addition of TPP-DNA) was 370±20-fold, compared to the value observed for the corresponding single-quencher probes (61-fold). The fluorescence turn-on value results from low initial fluorescence of 2-STAR probes, which is reduced by a more than a factor of 6 relative to Q-STAR probes. This difference can be attributed in part to the presence of two dabsyl moieties, which quench the fluorophore with >99.7% efficiency.

To evaluate the role of probe exchange, we investigated the activation of 2-STAR probes by the longer 15-mer (ml) TPP probe (FIG. 13). Results showed that the rate of fluorescence activation of 2-STAR EC by ml TPP-DNA was lower than that for ms TPP-DNA. This finding confirms that slow exchange of TPP-DNA probes impedes two successive binding/reaction events and presumably causes substantial accumulation of non-fluorescent mono-quencher intermediates. This result provides evidence that probe exchange provides for efficient fluorescence turn-on of 2-STAR probes by single TPP-DNAs. Additionally, the results indicate that both quenchers are released to achieve fluorescence activation.

To assess sequence specificity, the activation of 2-STAR EC fluorescence over time was monitored using SE-DNA as a single mismatch-containing template (FIG. 13). The effect of the single mismatch on fluorescence activation was observed: after 115 min, the fluorescence emission generated by ms TPP-DNA and the mismatched template reached 0.9±0.2% of the value for the complementary EC-DNA template. By comparison, the corresponding value for the control single-quencher probes was 11.0±1.8% for the same mismatched target under similar conditions. Therefore, double displacement probes improve the single mismatch specificity for this set of probes by a factor of more than 10. The fluorescence generated by the off template reaction of 2-STAR EC and ss TPP-DNA (i.e., template DNA omitted) was as low as (or slightly lower than) that with the singly mismatched template. The results indicate that double quencher release probes enhance the sequence-specificity and turn-on value of templated fluorescence schemes, and suppress off-template reaction signals.

FIG. 13 shows a kinetic analysis of template-mediated fluorescence activation of 2-STAR EC by DNA probes with a single triphenylphosphine (TPP) modification. Two TPP-DNA probes of different sequence length were investigated at 37° C.: ms TPP-DNA (solid lines) or ml TPP-DNA (dashed lines). Template dependence was observed by incubating the probes with the matched template EC-DNA (red traces), the mismatched template SE-DNA (blue traces) and without template (green traces).

Figure 14:
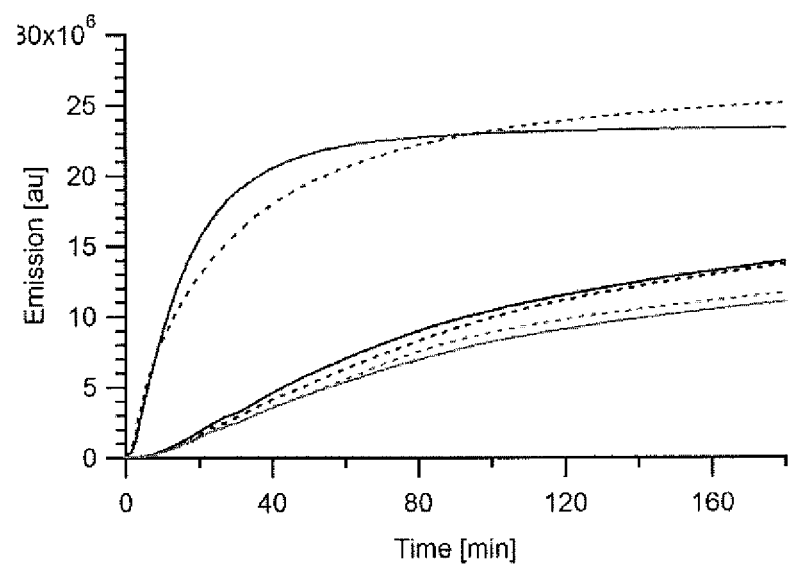
FIG. 14. Kinetic analysis of template-mediated fluorescence activation of 2-STAR EC by DNA probes with two triphenylphosphine (TPP) modifications and different sequence lengths: ds TPP-DNA (solid lines) and dl TPP-DNA (dashed lines) (matched template EC-DNA, red traces; mismatched template SE-DNA, blue traces; no template, green traces).

Fluorescence activation of 2-STAR probes with dual TPP-DNAs. Since two independent reductions are required for 2-STAR activation, fluorescence activation by a single probe carrying two reducing groups was investigated. Dual TPP-DNA probes obviate probe exchange, because the release of both quenchers may be carried out with a single probe-binding event. Moreover, in certain applications where probe exchange may be impractical, dual TPP-DNA probes can be used particularly if high-affinity probe binding is necessary. Therefore, the ability of dual-TPP-DNA probes (ds or dl) to activate 2-STAR probes in a template-dependent configuration was evaluated. Under the same conditions described above, incubation of 2-STAR EC (100 nM) with ds TPP-DNA (300 nM) and the EC-DNA (100 nM) template provided a strong fluorescence turn-on signal (FIG. 14). Fluorescence activation was slightly more rapid for ds TPP-DNA than for ms TPP-DNA, and no evident lag phase was observable for ds/dl TPP-DNAs. The experiment with longer 15-mer (dl) TPP-DNA probes provided similar kinetic traces as 9-mer (ds) TPP-DNA, which indicates that fluorescence activation was independent of strand exchange. Probe activation for 15-mer dl TPP-DNA was decelerated relative to ds TPP-DNA after approximately 50% conversion. Partial oxidation of the bis-triphenylphosphine probes during conjugation, purification and storage may account for incomplete probe activation without strand exchange.

By comparison with mono TPP-DNAs, which yielded extremely little background signal without template, the dual-TPP probes yielded some off-template background signal and lower selectivity against a singly mismatched template (SE-DNA). The off-template signal was 40-fold higher than with mono TPP-DNA probe after 115 min (FIGS. 13 and 14) and after 115 min the mismatch specificity was 2.3±0.7-fold for 2-STAR EC and ds TPP-DNA. Decreased mismatch specificity and higher off-template reaction for dual TPP-DNA probes was anticipated because both quenchers of a 2-STAR probe can be released in a single reaction event. The background reaction exceeds that of single-quencher Q-STAR probes with single TPP-DNA. Therefore, dual TPP-DNA probes generate increased background reaction at least in part by an alternate mechanism.

FIG. 14 illustrates a kinetic analysis of template-mediated fluorescence activation of 2-STAR EC by DNA probes with two triphenylphosphine (TPP) modifications. Two dual TPP-DNA probes of different sequence length were investigated: ds TPP-DNA (solid lines) or dl TPP-DNA (dashed lines). Template dependence was assessed by incubating the probes with the matched template EC-DNA (red traces), the mismatch containing template SE-DNA (blue traces) and without template (green traces).

Figure 15:
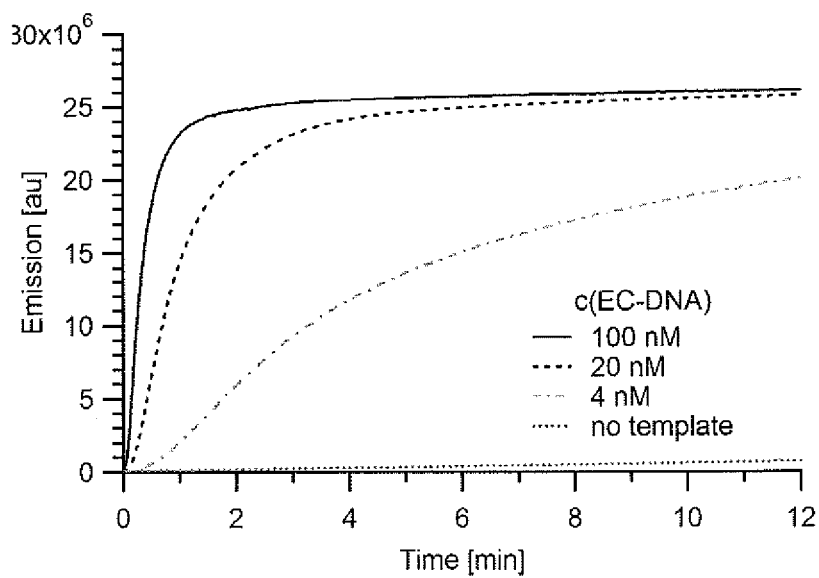
FIG. 15. Signal amplification for 2-STAR EC with substoichiometric concentrations of the target EC-DNA.

2-STAR probes provide amplified detection signal with reduced background reaction. Probes for DNA template-mediated fluorescence activation have been shown to generate amplified reporter signals when the target concentration is below the probe concentration, by an isothermal catalytic cycle of target binding, reaction, and dissociation (Grossmann, T. N., Strohbach, A. and Seitz, O. ChemBioChem 2008, 9, 2185-2192). In Example 1, Q-STAR probes yielded signal amplification of approximately >75-fold. The performance of 2-STAR probes under turnover conditions was evaluated by incubating 2-STAR EC (100 nM) and ss TPP-DNA (600 nM) with EC-DNA target (100 nM, 20 nM, and 4 nM) and measuring the intensity of fluorescence as a function of time (FIG. 15). Within a few hours, the fluorescence emission for the substoichiometric concentrations of EC-DNA approached the level of complete probe activation, indicating that 2-STAR probes are able to provide an amplified signal corresponding to at least 20 turnovers. The generation of an amplified signal was slower for 2-STAR probes than for Q-STAR probes, and this trend increased as the concentration declined. In particular, the delay phase associated to the accumulation of single-displacement intermediates lengthened with decreasing target concentrations. Although signal amplification was reduced for 2-STAR compared to Q-STAR probes in the experimental time interval, this effect was compensated for by an overproportional decline of the background reaction between 2-STAR EC with ms TPP-DNA relative to Q-STAR EC. For example, after 12 h, the fluorescence of 2-STAR EC in the absence of template reached 3.0±1.0% of the value measured for complete conversion, compared to 17.0±1.6% for Q-STAR probes. Thus, the data shows that the 2-STAR probe provides an amplified reporter signal with a higher S/B ratio than the corresponding single quencher probe.

FIG. 15 illustrates the signal amplification for 2-STAR EC with substoichiometric concentrations of the target EC-DNA (conditions are same as in FIG. 13).

Specificity enhancing effect of 2-STAR probes for weakly destabilizing mismatches.

Figure 16:
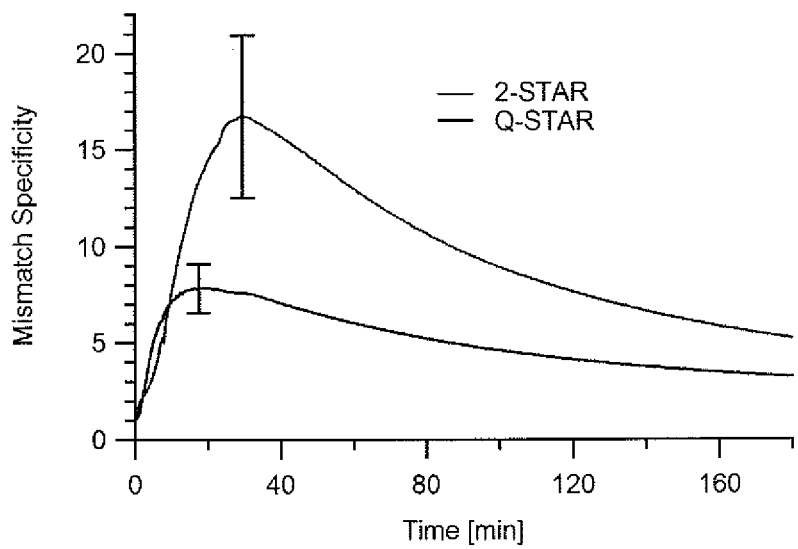
FIG. 16. Comparison of single nucleotide discrimination of 2-STAR SE and Q-STAR SE for a weakly destabilizing A-G mismatch (matched template SE-DNA versus mismatched template EC-DNA).

The experiments with the T-C mismatch-containing SE-DNA template illustrate that probes relying on two quencher release events provide enhanced sequence discrimination. Because some mismatches are less destabilizing (and thus more difficult to discriminate) than C-T (Aboul-ela, F.; Koh, D.; Tinoco, I., Martin, F. H. Nucleic Acids Res. 1985, 13, 4811-4824), the specificity-enhancing properties of 2-STAR probes for a weakly destabilizing A-G mismatch were assessed. A second 2-STAR probe (2-STAR SE) complementary to the 16S rRNA sequence of Salmonella enterica was prepared and assessed in combination with ms TPP-DNA to discriminate between the complementary target (SE-DNA) and the corresponding sequence of E. coli (EC-DNA), which contains a mismatch site (Table 2). The minor difference in thermal stability between the matched (A-T base pair) and the mismatched (A-G mispair) duplex has rendered sequence selectivity difficult in previous studies (Li, X. and Liu, D. R. Angew. Chem., Int. Engl. Ed. 2004, 43, 4848-4870). Incubation of the control Q-STAR SE (100 nM) with ms TPP-DNA (600 nM) with either the matched SE-DNA or the mismatched EC-DNA (100 nM) provided moderate selectivity; the fluorescence signal generated after 115 min in the presence of the mismatched target EC-DNA reached 23±7% of that of the matched target. In comparison, the EC-DNA template-mediated reaction of 2-STAR SE was decelerated relative to the background reaction of Q-STAR SE, providing 12±4% background signal relative to the matched target. To analyze this difference quantitatively over time, the sequence specificity of 2-STAR SE and Q-STAR SE was calculated by plotting the fluorescence emission of the reaction with SE-DNA divided by that with EC-DNA as a function of time (FIG. 16). With this mismatch, the 2-STAR probes reached a sequence selectivity of 16±4-fold after 29.5 min. In comparison, the sequence selectivity for Q-STAR peaked earlier (17.5 min) and maximized at a value of 7.8±1.3 fold.

FIG. 16 illustrates the single nucleotide discrimination of 2-STAR SE and Q-STAR SE for a weakly destabilizing A-G mismatch. Sequence specificity was calculated by dividing the fluorescence intensity for the reaction mediated by the matched template SE-DNA by the fluorescence intensity for the reaction mediated by the mismatched template EC-DNA. Error bars represent standard deviation of the mismatch sensitivity at the time point of maximal specificity.

Thermal stability of 2-STAR probes. In water, α-azidoether groups can disintegrate over an extended timeframe (Hassner, A.; Fibiger, R.; Amarasekara, A. S. J. Org. Chem. 1988, 53, 22-27; Amyes, T. L.; Jencks, W. P. J. Am. Chem. Soc. 1989, 111, 7888-7900), which would lead to background fluorescence for Q-STAR probes from non specific probe activation during an experiment or after storage. Although the stability of Q-STAR probes at physiological conditions is adequate, at elevated temperatures it was observed that probes undergo nonspecific quencher release. The effect of double release probes on the thermal stability was evaluated by comparing the fluorescence level of 2-STAR SE and Q-STAR SE probes after incubation in buffer for 90 min at various temperatures and normalizing to the fluorescence level for complete fluorescence activation. At ambient temperatures, neither probe showed a significant increase in background fluorescence over 90 min. At higher temperatures the fluorescence level intensified. For example, Q-STAR SE incubated for 90 min at 85° C. exhibited a fluorescence level corresponding to 13.5±1.3% probe activation. Fluorescence was lower for 2-STAR SE, reaching 3.6±0.4% conversion under the same conditions, indicating that the 2-STAR probe has reduced background fluorescence during prolonged incubation at elevated temperatures.

Figure 17:
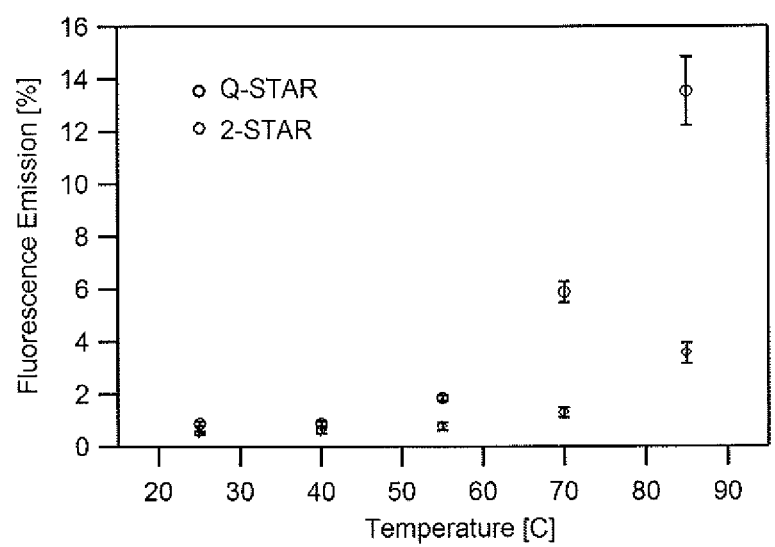
FIG. 17. Comparison of the thermal stability of 2-STAR and Q-STAR probes.

FIG. 17 illustrates the thermal stability of 2-STAR and Q-STAR probes. The quenched probes were incubated in buffer for 90 min at different temperatures. Fluorescence emission (y-axis) indicates the fluorescence intensity of the samples as a percentage of fluorescence intensity of completely converted 2-STAR probes.

Materials and Methods

Chemicals and reagents. Anhydrous solvents were purchased from Fisher Scientific and used without further purification. Chemicals were purchased from either Sigma-Aldrich or Acros and used without further purification. Reagents used for the solid-phase synthesis of oligonucleotides such as phosphoramidites, solid-supports, amino-modifiers, and synthesizer reagent-solutions were acquired from Glen Research. Bioreagents were purchased from VWR, and cell cultures from ATCC.

Instrumentation. $^1$H- and $^{13}$C-NMR spectra were recorded on a Varian Innova 500 MHz NMR or a Mercury 400 MHz NMR spectrometer. $^1$H- and $^{13}$C-NMR spectra were internally referenced to the residual solvent signal. High resolution mass spectrometry analysis was performed by the UC Riverside Mass Spectrometry Facility. Analytical and semi-preparative high performance liquid chromatography was performed on a LC-CAD Shimadzu liquid chromatograph, equipped with a SPD-M10A VD diode array detector and a SCL 10A VP system controller. Fluorescence measurements were performed on a Fluorolog 3 Jobin Yvon fluorophotospectrometer equipped with an external temperature controller. Oligonucleotide masses were determined by the Stanford University Protein and Nucleic Acid Facility using a Perspective Voyager-DE RP Biospectrometry MALDI-TOF mass-spectrometry instrument using a 3-hydroxypicolinic acid/di-ammonium hydrogen citrate matrix. Bacterial imaging was performed on a Nikon Eclipse E800 epifluorescence microscope equipped with a Nikon Plan AP 100×/1.40 oil immersion objective and a SPOT RT digital camera.

Bacteria culture. Growth medium (Luria-Bertani), and glass containers were sterilized by autoclaving at 120° C. for 20 min. E. coli K12 and Salmonella enterica were acquired from ATCC (catalog numbers 10798 and 700720 for E. coli and Salmonella enterica, respectively). Bacteria cultures were grown to mid-log phase in Luria-Bertani medium at 37° C.

Mammalian cell culture. HL-60 cells (American Type Culture Collection) were grown in DMEM without phenol red and containing 10% FBS, 1 U/mL non-essential amino acids, 50 units/ml penicillin, and 50 μg/ml streptomycin. They were passaged in 75-cm$^2$ culture flasks. Cells were maintained at 37° C. in an atmosphere of 5% $CO_2$ at $1\times10^5$ cells/ml and within 0-20 passages after purchasing from the supplier.

Synthetic Procedures

Scheme 1, Synthesis of the α-Azidoether Linker

N-(3-hydroxypropyl)trifluoroacetamide (3)

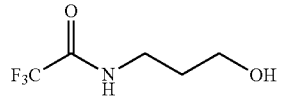 [SMILES: O=C(NCCCO)C(F)(F)F]

Ethyl trifluoroacetate (14.1 g; 0.1 mol) was added dropwise to 3-amino-1-propanol (6 g; 0.08 mol) cooled to 0° C. The mixture was stirred at 0° C. for 60 min; the completion of the reaction was confirmed by a negative Ninhydrin test. Volatiles were removed by rotary evaporation and the residue purified by vacuum distillation to provide N-(3-hydroxypropyl)trifluoroacetamide as a clear, viscous liquid in a yield of 13.4 g (98%). $^1$H-NMR (500 MHz, CDCl$_3$): δ=3.52-3.57 ppm (m, 2H), 2.17 ppm (bs, 1H), 3.54 ppm (dt, J=6.0, 6.0 Hz, 2H), 3.81 ppm (t, J=5.5 Hz, 2H), 7.28 ppm (bs, 1H), $^{13}$C-NMR (500 MHz, CDCl$_3$): δ=30.42, 38.35, 61.05, 115.93 ppm (q, J=1142 Hz), 157.76 ppm (q, J=150 Hz).

N-(3-oxopropyl)trifluoroacetamide (4)

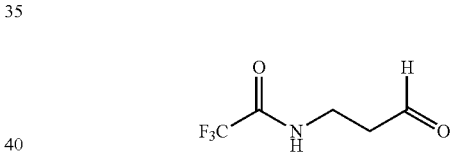

To a solution of N-(3-hydroxypropyl)trifluoroacetamide (1.6 g, 9.3 mmol) in anhydroud DCM (10 mL) cooled to 0° C. was added a solution of Dess-Martin periodinane (30 mL of 15 wt % in DCM; 14 mmol). Stirring was continued at 0° C. for 10 min, then the mixture was allowed to warm to room temperature and stirring was continued for 2 h. The mixture was poured onto a biphasic mixture of saturated aqueous NaHCO$_3$ (60 mL) and Et$_2$O (60 mL) and stirred vigorously for 20 min. The forming precipitate was eliminated by filtration and the layers separated. The aqueous layer was extracted with Et$_2$O. The combined organic layers were washed with brine, dried (MgSO$_4$), filtrated, and evaporated. The product was purified by column chromatography (Hex: EtOAc 3:2) to provide N-(3-oxopropyl)trifluoroacetamide as a viscous liquid in a yield of 0.82 g (52%). The product decomposes at room temperature and was used within 24 h of preparation. $^1$H-NMR (500 MHz, CDCl$_3$): δ=2.84 ppm (t, J=6.0 Hz, 2H), 3.64 ppm (dt, J=6.0, 6.0 Hz, 2H), 6.98 ppm (bs, 1H), 9.81 ppm (s, 1H); $^{13}$C-NMR (500 MHz, CDCl$_3$): δ=33.36, 42.58, 115.74 ppm (q, J=1144 Hz), 157.42 ppm (q, J=146.5 Hz), 200.85 ppm.

Methyl 4-[(trimethylsiloxy)methyl]benzoate (5)

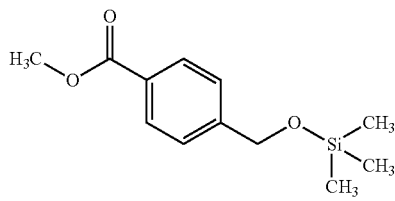

Chlorotrimethylsilane (2.3 mL, 18.4 mmol) was added dropwise to a solution of methyl 4-(hydroxymethyl)benzoate (2.0 g, 12.0 mmol) and triethylamine (3.3 mL, 23.7 mmol) in anhydrous THF (80 ml) cooled to 0° C. A precipitate formed and the stirring was continued at 0° C. for 1 h. The mixture was diluted with hexanes (50 mL) and precipitates eliminated by vacuum filtration through a sintered funnel. Volatiles were removed by rotary evaporation. The residue was purified by flash chromatography (DCM:Hex 1:1+1% TEA) through a short silica column providing methyl 4-[(trimethylsiloxy)methyl]benzoate as a clear liquid in a yield of 2.5 g (87%). $^1$H-NMR (500 MHz, CDCl$_3$): δ=0.16 ppm (s, 9H), 3.90 ppm (s, 3H), 4.74 ppm (s, 2H), 7.38 ppm (d, J=8.0 Hz, 2H), 8.00 ppm (d, J=8.0 Hz, 2H); $^{13}$C-NMR (500 MHz, CDCl$_3$): δ=−0.41, 52.09, 64.12, 126.08, 128.90, 129.68, 146.39, 167.10 ppm. HRMS [+Scan]; calculated m/z for C12H19O3Si 239.1098; observed mass: 239.1095.

Methyl 4-[(1-azido-3-trifluoroacetamidopropoxy)methyl]benzoate (6)

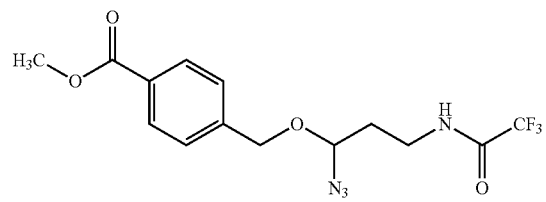 [SMILES: COC(=O)c1ccc(COC(CCNC(=O)C(F)(F)F)N=[N+]=[N-])cc1]

A solution of azidotrimethylsilane (0.93 mL; 7.1 mmol) and methyl 4-[(trimethylsiloxy)methyl]benzoate (1.35 g; 5.7 mmol) in anhydrous MeCN (3 mL) was added dropwise to a solution of N-(3-oxopropyl)trifluoroacetamide (0.8 g; 4.7 mmol) containing a catalytic amount of anhydrous ferric chloride (38 mg; 0.2 mmol) in anhydrous MeCN (10 mL) cooled to −40° C. The mixture was stirred at −40° C. for 90 min and the reaction quenched with phosphate buffered saline (pH 7.4). The aqueous phase was extracted with DCM. The combined organic layers were washed with brine, dried (MgSO4), filtrated and evaporated. The residue was purified by silica column chromatography (DCM:Hex:EtOAc, 6:3:1) and the methyl 4-[(3-amino-1-azidopropoxy)methyl]benzoate was obtained as a clear viscous liquid, which solidified upon prolonged standing in a yield of 0.95 g (56%). $^1$H-NMR (500 MHz, CDCl$_3$): δ=2.04-2.14 ppm (m, 2H), 3.40-3.47 ppm (m, 1H), 3.56-3.64 ppm (m, 1H), 3.92 ppm (s, 3H), 4.63 ppm (d, J=12.0 Hz, 1H), 4.66 ppm (dd, J=6.0, 4.5 Hz, 1H), 4.90 ppm (d, J=12.0 Hz, 1H), 6.89 ppm (bs, 1H, NH), 7.41 ppm (d, J=8.5 Hz, 2H), 8.04 ppm (d, J=8.5 Hz, 2H); $^{13}$C-NMR (500 MHz, CDCl$_3$): δ=33.94, 35.83, 52.29, 70.66, 90.46, 115.76 ppm (q, J=1146.5 Hz), 127.76, 130.02, 130.14, 141.30, 157.23 (q, J=148.0 Hz), 166.79 ppm. HRMS [+Scan]; calculated m/z for C12H19O3Si 239.1098; observed mass: 239.1095.

Methyl 4-[(3-amino-1-azidopropoxy)methyl]benzoate (1)

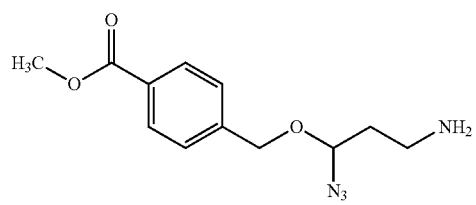 [SMILES: COC(=O)c1ccc(COC(CCN)N=[N+]=[N-])cc1]

Methyl 4-[(1-azido-3-trifluoroacetamidopropoxy)methyl]benzoate (220 mg; 0.61 mmol) was added to methanol (2.3 mL) and a solution of potassium carbonate (200 mg; 1.4 mmol) in H$_2$O (1.1 mL). The mixture was vigorously stirred at room temperature for 3 h, diluted with water and extracted with EtOAc. The combined organic layers were washed with brine, dried (MgSO$_4$), filtrated and evaporated. The residue was purified by silica column chromatography (DCM:MeCN 1:1+5% MeOH+1% TEA) to provide methyl 4-[(3-amino-1-azidopropoxy)methyl]benzoate as a liquid in a yield of 110 mg (68%). $^1$H-NMR (500 MHz, CDCl$_3$): δ=1.78-2.02 ppm (m, 2H), 2.85 ppm (t, J=7.0 Hz, 2H), 3.91 ppm (s, 3H), 4.60 ppm (t, J=6.5 Hz, 1H), 4.62 ppm (d, J=12.5 Hz, 1H), 4.87 ppm (d, J=12.5 Hz, 1H); $^{13}$C-NMR (500 MHz, CDCl$_3$): δ=37.79 (in [D6]DMSO this peak splits in two distinct signals with δ=37.92 ppm and 38.93 ppm), 52.21, 70.16, 90.40, 127.55, 129.80, 129.89, 142.17, 166.84 ppm. HRMS [+Scan]; calculated m/z for C12H17N4O3 265.1295; observed mass: 265.1292.

Methyl 4-[(1-azido-3-dabsylsulfonamidopropoxy)methyl]benzoate (7)

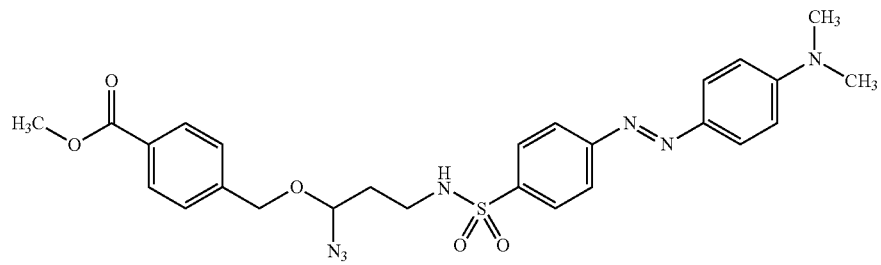

Dabsyl chloride (0.3 g; 0.93 mmol) was added to a solution of methyl 4-[(3-amino-1-azidopropoxy)methyl]benzoate (0.2 g; 0.76 mmol) and triethylamine (0.21 mL; 1.51 mmol)

cooled to 0° C. The mixture was stirred at ambient temperature for 1 h and evaporated. The residue was purified by silica column chromatography (DCM:Hex, 4:1+1% TEA) to provide methyl 4-[(1-azido-3-dabsylsulfonamidopropoxy)methyl]benzoate as a dark orange gum in a yield of 360 mg (86%). $^1$H-NMR (500 MHz, CDCl$_3$): δ=1.95-2.10 ppm (m, 2H), 3.08-3.13 ppm (m, 1H), 3.13 ppm (s, 6H), 3.17-3.20 ppm (m, 1H), 3.91 ppm (s, 3H), 4.59 ppm (d, J=12.0 Hz, 1H), 4.61 ppm (t, J=5.0 Hz, 1H), 4.84 ppm (d, J=12.0 Hz, 1H), 6.77 ppm (d, J=9.5 Hz, 2H), 7.38 ppm (d, J=8.5 Hz, 2H), 7.89-7.93 ppm (m, 6H), 8.04 ppm (d, J=8.0 Hz, 2H); $^{13}$C-NMR (500 MHz, CDCl$_3$): δ=34.30, 39.17, 40.34, 52.23, 70.47, 89.98, 103.25, 111.48, 122.73, 125.82, 127.67, 128.06, 129.97, 138.96, 141.67, 143.58, 153.17, 155.76, 166.81 ppm. HRMS [+Scan]; calculated m/z for C26H30N7O5S 552.2024; observed mass: 552.2009.

4-[(1-azido-3-dabsylamidopropoxy)methyl]benzoic acid (2)

N-(4-hydroxybutyl)trifluoroacetamide (8)

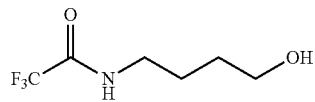

Ethyl trifluoroacetate (3.3 mL; 28 mmol) was added dropwise to cooled (0° C.) 4-amino-1-butanol (2.0 g; 22.4 mmol). The mixture was stirred for 2 h at 0° C. and evaporated. The clear liquid was dried on the high vacuum. The product was obtained in a yield of 4.1 g (99%). $^1$H-NMR (500 MHz, CDCl$_3$): δ=1.61-1.67 ppm (m, 2H), 1.68-1.74 ppm (m, 2H), 2.31 (bs, 1H), 3.38 ppm (dt, 2H), 3.72 ppm (t, 2H), 7.40 ppm (bs, 1H); $^{13}$C-NMR (500 MHz, CDCl$_3$): δ=26.02, 29.70, 40.01, 62.48, 116.20 ppm (q, J=1144.0 Hz), 157.66 ppm (q, J=146.5 Hz). HRMS [+Scan]; calculated m/z for C6H11NO2F3 186.0747; observed mass: 186.0741.

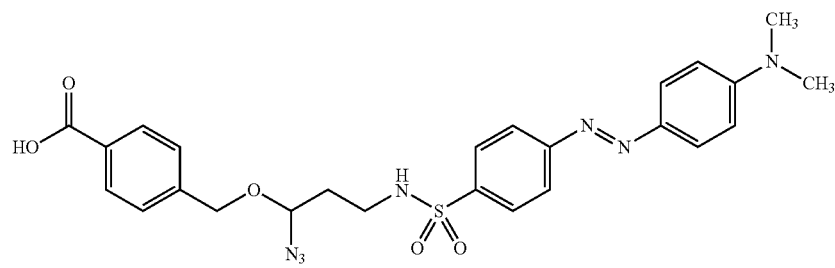 [SMILES: CN(C)c1ccc(/N=N/c2ccc(S(=O)(=O)NCCC(N=[N+]=[N-])OCc3ccc(C(=O)O)cc3)cc2)cc1]

A solution of lithium hydroxide monohydrate (290 mg; 6.9 mmol) in H$_2$O (2 mL) was added to a solution of methyl 4-[(1-azido-3-dabsylsulfonamidopropoxy)methyl]benzoate (290 mg; 0.53 mmol) in THF (2 mL). The biphasic mixture was stirred vigorously at ambient temperature for 5.5 h and quenched with 1 M aqueous AcOH (3 mL). The aqueous layer was extracted with EtOAc containing 10% MeOH, dried (Mg$_2$SO$_4$), filtered and evaporated onto silica (3 g). The product was obtained by silica column chromatography (DCM:MeCN 9:1+1% MeOH+0.5% AcOH) as a bright orange solid in a yield of 267 mg (94%). $^1$H-NMR (500 MHz, [D6]DMSO): δ=1.78-1.90 ppm (m, 2H), 2.85-2.95 ppm (dt, J=6.5, 6.5 Hz, 2H), 3.07 ppm (s, 6H), 4.62 ppm (d, J=12.0 Hz, 1H), 4.78 ppm (d, J=12.5 Hz, 1H), 4.83 ppm (t, J=6.0 Hz, 1H), 6.83 ppm (d, J=9.5 MHz, 2H), 7.41 ppm (d, J=8.5 Hz, 2H), 7.82 ppm (d, J=9.0 Hz, 2H), 7.90-7.95 ppm (m, 6H), 12.96 ppm (bs, 1H); $^{13}$C-NMR (500 MHz, [D6]DMSO): δ=34.09, 38.43, 69.73, 89.76, 111.61, 122.33, 125.47, 127.51, 127.89, 129.42, 130.13, 139.85, 142.22, 142.63, 153.13, 154.60, 167.12 ppm. HRMS [+Scan]; calculated m/z for C25H28N7O5S 538.1867; observed mass: 538.1871.

N-(4-oxobutyl)trifluoroacetamide (9)

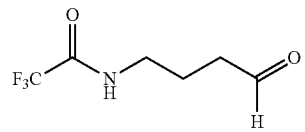 [SMILES: O=CCCCNC(=O)C(F)(F)F]

N-(4-hydroxybutyl)trifluoroacetamide (1.65 g; 8.9 mmol) was dissolved in anhydrous DCM (9 mL) and cooled to 0° C. A solution of Dess-Martin periodinane (15% in DCM; 30 mL; 14.0 mmol) was added to the cooled solution and stirred first at 0° C. for 10 min and then at room temperature for 2.5 h. The reaction was quenched with 1:1 10% sodium thiosulfate and saturated NaHCO$_3$ and the biphasic mixture vigorously stirred for 30 min. The layers were separated and the aqueous layer extracted with DCM. The combined organic layers were dried over MgSO$_4$, filtrated and evaporated. The residue was purified by column chromatography (Hex:EtOAc 2:1+1% MeOH) providing N-(4-oxobutyl)trifluoroacetamide in a yield of 1.15 mg (71%).

Methyl 4-[(1-azido-4-trifluoroacetamidobutoxy)methyl]benzoate (10)

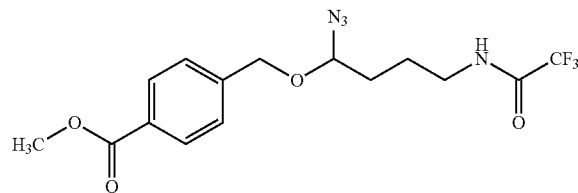 [SMILES: COC(=O)c1ccc(COC(CCCNC(=O)C(F)(F)F)N=[N+]=[N-])cc1]

A solution of N-(4-oxobutyl)trifluoroacetamide (1.0 g; 5.5 mmol) and a catalytic amount of anhydrous ferric chloride (44 mg; 0.27 mmol) in anhydrous MeCN (6 mL) was cooled to −40° C. A solution of methyl 4-[(trimethylsilyloxy)methyl]benzoate (1.56 g; 6.6 mmol) and azidotrimethylsilane (0.94 g; 8.2 mmol) in MeCN (5 mL) was added dropwise to the cooled solution. The reaction mixture was stirred at −40° C. for 60 min and quenched with buffered phosphate saline (pH 7.2). The aqueous solution was extracted with Et$_2$O. The organic layer was washed with brine, dried over MgSO$_4$, filtrated and evaporated. The residue was purified by column chromatography (Hex:DCM:EtOAc 7:2:1) to provide methyl 4-[(1-azido-4-trifluoroacetamidobutoxy)methyl]benzoate in a yield of 0.95 g (46%).

$^1$H-NMR (500 MHz, CDCl$_3$): δ=1.72-1.78 ppm (m, 2H), 1.83-1.90 ppm (m, 2H), 3.36-3.44 ppm (m, 2H), 3.92 ppm (s, 3H), 4.51 ppm (t, J=6.0 Hz, 1H), 4.62 ppm (d, J=12.5 Hz, 1H), 4.88 ppm (d, J=12.0 Hz, 1H), 6.50 ppm (bs, 1H), 7.41 ppm (d, J=8.0 Hz, 2H), 8.04 ppm (d, J=8.0 Hz, 2H); $^{13}$C-NMR (500 MHz, CDCl$_3$): δ=21.14, 31.71, 39.42, 52.27, 70.35, 91.70, 115.85 ppm (q, J=1146.5 Hz), 127.69, 129.96, 141.80, 157.40 ppm (q, J=146.5 Hz), 166.86 ppm.

HRMS [+Scan]; calculated m/z for C15H21N5O4F3 392.1540; observed mass: 392.1543.

Methyl 4-[(4-amino-1-azidobutoxy)methyl]benzoate (11)

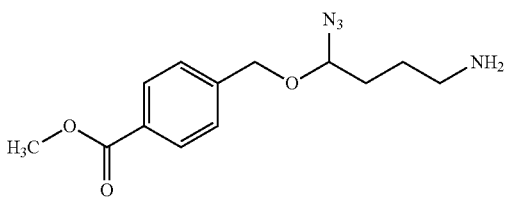 [SMILES: COC(=O)c1ccc(COC(CCCN)N=[N+]=[N-])cc1]

To a solution of methyl 4-[(1-azido-4-trifluoroacetamidobutoxy)methyl]benzoate (0.4 g; 1.1 mmol) in MeOH (4.6 mL) was added a solution of potassium carbonate (0.4 g; 2.9 mmol) in water (2.4 mL) and stirred at room temperature for 4 h. The mixture was diluted with water and extracted with EtOAc. The organic layers were combined, dried over MgSO$_4$, filtrated and evaporated. The residue was purified by column chromatography (MeCN+5% MeOH) to provide methyl 4-[(4-amino-1-azidobutoxy)methyl]benzoate in 0.19 g yield (65%).

$^1$H-NMR (500 MHz, CDCl$_3$): δ=1.51-1.69 ppm (m, 2H), 1.77-1.91 ppm (m, 2H), 2.70 ppm (bs, 2H), 2.74 ppm (t, J=7.0 Hz, 2H), 3.90 ppm (s, 3H), 4.45 ppm (t, J=6.0 ppm, 1H), 4.60 ppm (d, J=12.5 Hz, 1H), 4.86 ppm (d, J=12.5 Hz, 1H), 7.41 ppm (d, J=8.5 Hz, 2H), 8.02 ppm (d, J=8.0 Hz, 2H); $^{13}$C-NMR (500 MHz, CDCl$_3$): δ=27.95, 31.90, 41.34, 52.21, 70.12, 91.77, 127.55, 129.76, 129.87, 142.19, 166.87 ppm.

Methyl 4-[(1-azido-4-(3-Black hole quencher 2-propionamido)butoxy)methyl]benzoate (12)

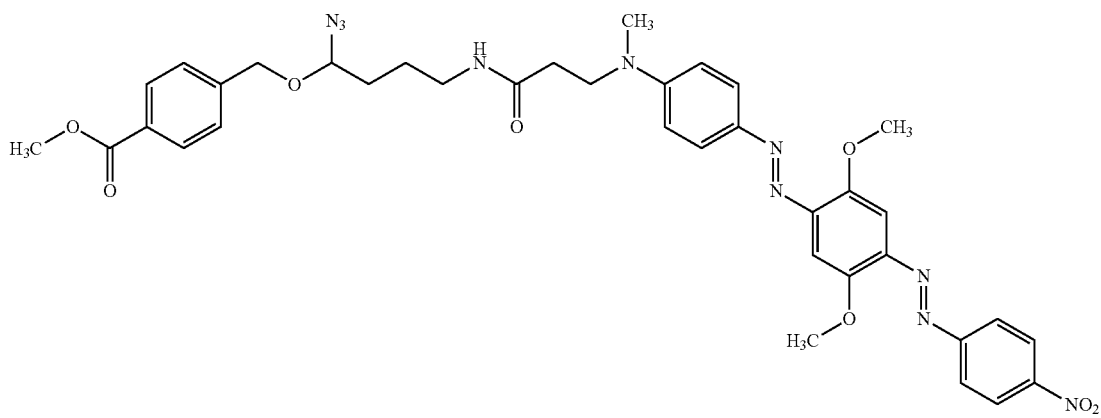 [SMILES: COC(=O)c1ccc(COC(CCCNC(=O)CCN(C)c2ccc(/N=N/c3cc(OC)c(/N=N/c4ccc([N+](=O)[O-])cc4)cc3OC)cc2)N=[N+]=[N-])cc1]

A solution of Black hole quencher 2 propionic acid (255 mg; 0.52 mmol), O-(Benzotriazol-1-yl)-N,N,N',N'-tetramethyluronium hexafluorophosphate (196 mg; 0.52 mmol) and diisopropylethylamine (134 mg; 1.03 mmol) in anhydrous DMF (7 mL) was added to methyl 4-[(4-amino-1-azidobutoxy)methyl]benzoate (0.12 g; 0.43 mmol). The mixture was stirred at room temperature for 30 min. The solvent was evaporated and the residue dissolved in DCM and washed twice with brine. The organic layer was dried over MgSO₄, filtrated and evaporated. The residue was purified by silica column chromatography (DCM:MeCN 9:1+1% MeOH) to provide (12) in a yield of 195 mg (60%).

¹H-NMR (500 MHz, CDCl₃): δ=1.51-1.69 ppm (m, 2H), 1.77-1.91 ppm (m, 2H), 2.70 ppm (bs, 2H), 2.74 ppm (t, J=7.0 Hz, 2H), 3.90 ppm (s, 3H), 4.45 ppm (t, J=6.0 ppm, 1H), 4.60 ppm (d, J=12.5 Hz, 1H), 4.86 ppm (d, J=12.5 Hz, 1H), 7.41 ppm (d, J=8.5 Hz, 2H), 8.02 ppm (d, J=8.0 Hz, 2H); ¹³C-NMR (500 MHz, CDCl₃): δ=27.95, 31.90, 41.34, 52.21, 70.12, 91.77, 127.55, 129.76, 129.87, 142.19, 166.87 ppm.

HRMS [+Scan]; calculated m/z for C37H41N10O8 753.3103; observed mass: 753.3111.

4-[(1-azido-4-(3-Black hole quencher 2-propionamido) butoxy)methyl]benzoaic acid (13)

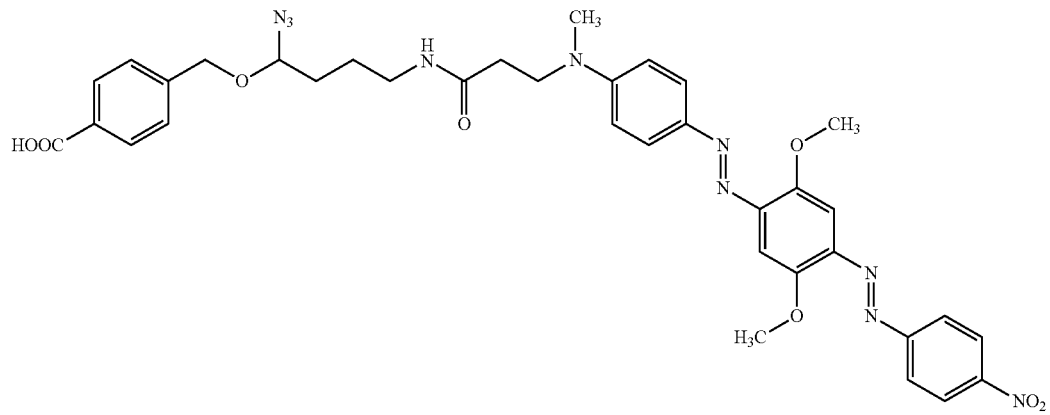 [SMILES: COc1cc(/N=N/c2ccc([N+](=O)[O-])cc2)c(OC)cc1/N=N/c1ccc(N(C)CCC(=O)NCCCC(N=[N+]=[N-])OCc2ccc(C(=O)O)cc2)cc1]

To a solution of 12 in THF (5 mL) was added a solution of lithium hydroxide monohydrate (320 mg; 7.6 mmol) in water (4 mL). The biphasic mixture was vigorously stirred at 40° C. for 5 h. The mixture was diluted with water, acidified with citric acid and extracted with DCM. The organic layer was washed with brine, dried over MgSO₄, filtrated and evaporated. 13 was obtained in a yield of 129 mg (83%). ¹H-NMR (500 MHz, [D6]DMSO): δ=1.43-1.50 ppm (m, 2H), 1.62-2.1.75 ppm (m, 2H), 2.38 ppm (t, J=8.5 Hz, 2H), 3.03 ppm (s, 3H), 3.06 ppm (q, 8.0 Hz, 2H), 3.715 ppm (t, 8.5 Hz, 2H), 3.94 ppm (s, 3H), 3.99 ppm (s, 3H), 4.66 ppm (d, J=16.0 Hz, 1H), 4.73 ppm (t, J=7.5 Hz, 1H), 4.81 ppm (d, J=15.5 Hz, 1H), 6.86 ppm (d, J=11.5 Hz, 2H), 7.37 ppm (s, 1H), 7.44 ppm (s, 1H), 7.44 ppm (d, J=10.0 Hz, 2H), 7.81 ppm (d, J=12.0 Hz, 2H), 7.92 ppm (d, J=10.0 Hz, 2H), 8.01 ppm (t, 1H), 8.06 ppm (d, J=11.5 Hz, 2H), 8.46 ppm (d, J=11.5 Hz, 2H). HRMS [+Scan]; calculated m/z for C36H39N10O8 739.2947; observed mass: 739.2953.

MMt-protected 5'-bis-amino-modifier phosphoramidite

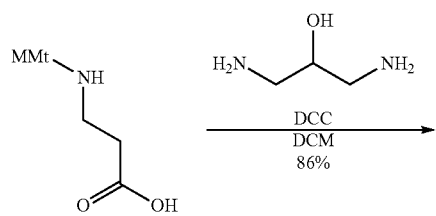

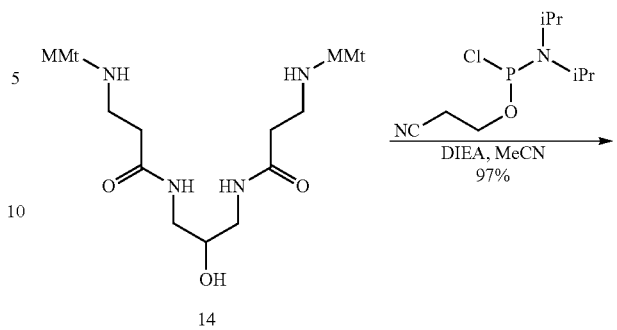

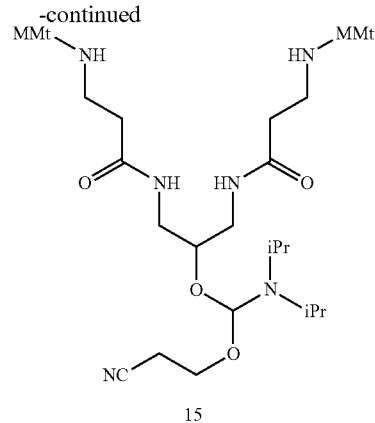

N,N-bis-[3-(4-monomethoxytritylamino)propionyl]-1,3-diamino-2-propanol (14). To a solution of N-(4-monomethoxytrityl)-β-alanine (Berube, G.; Richardson, V. J.; Ford, C. H. J. Synth. Commun. 1991, 21, 931-944) (1.45 g, 4.0 mmol) in anhyd. DCM (10 mL) was added N,N'-dicyclohexylcarbodiimide (0.82 g, 4.0 mmol) and 1,3-diamino-2-propanol (0.16 g, 1.8 mmol). A catalytic amount of 4-(dimethylamino)pyridine was added and the mixture stirred for 14 h at room temperature. The precipitated was eliminated by filtration and the product purified by silica column chromatography (Hex:EtOAc 2:3+0→5% MeOH+ 2% TEA) to provide N,N-bis-[3-(4-monomethoxytritylamino)propionyl]-1,3-diamino-2-propanol as a white foam in a yield of 1.2 g (86%). $^1$H-NMR (500 MHz, CDCl$_3$): δ=2.36 ppm (t, J=6.0 Hz, 4H), 2.46 ppm (t, J=6.0 Hz, 4H), 3.24-3.30 ppm (m, 2H), 3.39-3.45 ppm (m, 2H), 3.76 ppm (s, 6H), 4.05-4.18 (m, 1H), 6.78 ppm (d, 9.0 Hz, 4H), 6.96 ppm (t, J=6.0 Hz, 2H), 7.17 ppm (t, J=7.5 Hz, 4H), 7.26 ppm (t, J=7.5 Hz, 8H), 7.42 ppm (d, J=8.0 Hz, 8H). $^{13}$C-NMR (500 MHz, CDCl$_3$): δ=37.13, 39.93, 42.86, 55.22, 70.52, 113.21, 126.38, 127.92, 128.52, 129.84, 137.85, 146.01, 157.94, 174.12 ppm. HRMS [+Scan]; calculated m/z for C$_{49}$H$_{53}$N$_4$O$_5$ 777.4011; observed m/z: 777.4014.

N,N-bis-[3-(4-monomethoxytritylamino)propionyl]-1,3-diamino-2-propanol cyanoethyl diisopropyl-phosphoramidite (15). To a solution of N,N-bis-[3-(4-monomethoxytritylamino)propionyl]-1,3-diamino-2-propanol (300 mg; 0.39 mmol) and diisopropylethylamine (168 μL; 0.97 mmol) in anhyd. MeCN (3 mL) was added 2-cyanoethyl-N,N-diisopropyl chlorophosphoramidite (183 mg; 0.77 mmol). The solution was stirred for 90 min at room temperature under an argon atmosphere and concentrated under vacuum. The residue was purified by silica column chromatography (Hex: EtOAc:MeCN 7:3:1+2% TEA) to provide N,N-bis-[3-(4-monomethoxytritylamino)propionyl]-1,3-diamino-2-propanol cyanoethyl diisopropyl-phosphoramidite as a white foam in a yield of 368 mg (97° A)). $^1$H-NMR (400 MHz, CDCl$_3$): δ=1.16-1.21 ppm (m, 12H), 2.35-2.55 ppm (m, 10H), 2.92-3.00 ppm (m, 1H), 3.08-3.19 ppm (m, 1H), 3.55-3.66 ppm (m, 2H), 3.70-3.82 ppm (m, 10H), 3.88-3.98 ppm (m, 1H), 6.71-6.81 ppm (m, 6H), 7.13-7.18 ppm (m, 4H), 7.22-7.27 ppm (m, 8H), 7.32-7.36 ppm (m, 4H), 7.43-7.46 ppm (m, 8H) $^{13}$C-NMR (400 MHz, CDCl$_3$): δ=20.45 (10.38), 24.72 (24.57), 37.30 (37.24), 39.96, 40.56, 43.16 (43.03), 55.12, 58.41 (58.20), 70.37, 113.06, 118.25, 126.17, 127.78, 128.49, 129.78, 138.04 (138.02), 146.19, 157.71, 172.74, 173.14 ppm. HRMS [+Scan]; calculated m/z for C$_{58}$H$_{70}$N$_6$O$_6$P 977.5089; observed m/z: 977.5106.

Preparation of Oligonucleotides and DNA-Conjugates

Unmodified oligonucleotides. Oligonucleotides were synthesized on a 1 μmol scale by an ABI model 392 synthesizer using standard β-cyanoethylphosphoramidite coupling chemistry. Removal of the protecting groups and cleavage from the CPG-support were carried out by incubation in concentrated aqueous NH$_4$OH solution at 55° C. for 14 h. The oligonucleotides were purified using Poly-Pak II cartridges. Oligonucleotide concentrations were determined by UV-absorbance using extinction coefficients derived by the nearest neighbor approximation. The identity of the strands was confirmed by MALDI-TOF mass spectrometry (Table 1).

TPP-DNA conjugates. The oligonucleotides were prepared by 5'->3' synthesis with a 5'-amino-modifier 5 appended to the 3'-terminus. Monomethoxy-trityl protecting groups were removed on the synthesizer using alternating cycles of deprotection reagent (3 trichloroacetic acid in DCM) and DCM washes. The CPG was added to a solution containing 4-(diphenylphosphino)benzoic acid (0.1 M), 1-ethyl-3-(3-dimethylaminopropyl) carbodiimide hydrochloride (0.1 M), and diisopropylethylamine (0.2 M) in DMF. The suspension was placed under vacuum, backfilled with argon and incubated at 37° C. for 2.5 h. The DMF was decanted, the resin washed twice with MeCN, dispersed in aqueous NH$_4$OH/MeNH$_2$ deprotection/cleaveage solution (1 ml) containing the sacrificial oxygen scavenger tris-(2-carboxyethyl)phosphine (4 mg) and incubated for 1.5 h at 55° C. Beads were eliminated by filtration, the solution concentrated on the Speed-vac to remove the volatile amines; TPP-DNA was purified by reverse phase HPLC. TPP-DNA is sensitive to oxidation by atmospheric oxygen; TPP-DNA stock solutions were stored under argon at -78° C. and used within two weeks after preparation to ensure maximal reactivity of the probes.

Q-Star probes. Oligonucleotides were synthesized with a 5'-amino-modifier 5 appended to the 5'-terminus. The monomethoxy-trityl protecting group was removed on the synthesizer using alternating cycles of deprotection reagent (3% trichloroacetic acid in DCM) and DCM washes. The solid support was added to a solution containing 2 (25 mM), benzotriazol-1-yl-oxytripyrrolidinophosphonium hexafluorophosphate (PyBOP, 25 mM), and diisopropylethylamine (50 mM) in DMF (500 μl) and gently shaken for 5 h protected from light. The DMF was decanted, the resin washed twice with MeCN, and dispersed in aqueous NH$_4$OH/MeNH$_2$ deprotection/cleaveage solution (1 ml) and incubated for 1.5 h at 55° C. Beads were eliminated by filtration and the oligonucleotide probes were purified by reverse phase HPLC. Although the azidoether linker is chiral, no separation of diastereomers was seen in the HPLC traces. Templated reactions revealed no apparent difference in rates of reaction of the two diastereomers (see FIGS. 3 and 4). Q-STAR probes containing TAMRA or Quasar 670 fluorophores were synthesized using ultraMILD phosphoramidites and deprotected/cleaved using 0.05 M potassium carbonate in MeOH.

Table 3 summarizes MALDI-TOF mass spectrometry data ($^a$The molecular peak of TPP-DNA is accompanied by a major peak+16 m/z which was assigned to oxidation of the triphenylphosphine moiety during mass-spec sample preparation and measurement).

TABLE 3

| Strand | Calculated mass (m/z) | Observed mass (m/z) |
|---|---|---|
| Green STAR | 3615.8 | 3615.8 |
| Red STAR | 4264.0 | 4263.7 |
| TPP-DNA $^a$ | 3081.6 | 3080.2 |
| TPP-DNA * $^a$ | 4983.9 | 4983.2 |
| EC DNA | 6544.1 | 6539.9 |
| SE DNA | 6519.1 | 6514.6 |
| H1 | 5518.9 | 5521.0 |
| H2 | 5442.9 | 5540.7 |

2-Star probes. Oligonucleotides were synthesized with the 5'-diamino-modifier (15) appended to the 5'-terminus. MMt-trityl protecting groups were removed on the DNA synthesizer using alternating cycles of deprotection reagent (3% trichloroacetic acid in DCM) and DCM washes. The solid support was added to a solution containing the acid 2 (25 mM), benzotriazol-1-yl-oxytripyrrolidinophosphonium hexafluorophosphate (PyBOP, 25 mM), and diisopropylethylamine (50 mM) in DMF (250 μL) and gently shaken at room temperature for 5 h protected from light. The DMF was decanted, the resin washed twice with DMF and three times with MeCN, and dispersed in aqueous NH$_3$/MeNH$_2$ deprotection/cleaveage solution (1 mL) and incubated for 1 h at 55° C. Beads were removed by filtration and the oligonucleotide probes were purified by reverse phase HPLC. Templated reactions revealed no apparent difference in rates of reaction of the two diastereomers. The purity of the Q-STAR probes was assessed by analytical HPLC and found to be >95% with a minor impurity that contains two dabsyl and one fluorescein molecules.

Dual TPP-DNA conjugates. Oligonucleotides were prepared by 5'→3' synthesis using the 5'-bis-amino-modifier 15 as the terminal phosphoramidite for modification of the 3'-terminus. MMt-protecting groups were removed on the synthesizer using alternating cycles of deprotection reagent (3% trichloroacetic acid in DCM) and DCM washes. The CPGs were added to a solution containing 4-(diphenylphosphino)benzoic acid (0.1 M), 1-ethyl-3-(3-dimethylaminopropyl)carbodiimide hydrochloride (0.1 M), and diisopropylethylamine (0.2 M) in DMF (500 μL). Air trapped by the CPGs was removed by briefly vacuumizing the mixture followed by backfilling with argon. The reaction mixture was gently shaken for 2.5 h at room temperature. DMF was decanted, the resin washed twice with DMF and three times with MeCN, dispersed in aqueous $NH_4OH/MeNH_2$ deprotection/cleaveage solution (1 mL) containing the sacrificial oxygen scavenger tris-(2-carboxyethyl)phosphine (4 mg) and incubated for 1 h at 55° C. CPGs were removed by filtration, the solution concentrated (60 min) on the Speed-vac to remove the volatile amines. Dual TPP-DNAs were purified by semi-preparative reverse phase HPLC concentrated on the Speed-Vac, divided in aliquots, flushed with argon and stored at −78° C. Samples were used within one month after preparation to ensure maximal reactivity of the probes.

Experimental Procedures

Templated Fluorescence Activation Time-courses. Q-STAR probes (200 nM) and the corresponding template (200 nM unless stated otherwise) were incubated at 37° C. in tris-borate buffer (70 mM, pH 7.55) containing $MgCl_2$ (10 mM). TPP-DNA (600 nM) was added and the fluorescence emission ($\lambda ex=494$ nM; $\lambda em=521$ nm for green STAR and $\lambda em=580$ nm for red STAR) measured as function of time.

Bacterial Imaging. Bacterial cells were grown to mid-log phase. Aliquots (100-200 μL) were centrifuged and the supernatant decanted. Pellets were washed with 1×PBS buffer (pH 7.4) and resuspended in 6×SSC buffer (pH 7.4) containing 0.05% SDS. Q-STAR probes (200 nM), TPP-DNA (2 μM), and helper DNAs (3 μM) were added and the samples incubated at 37° C. without shaking and protected from light. Aliquots of incubated bacteria suspension were mixed with 2% agarose solution and spotted on cover slides without washing or fixation.

Flow cytometric analysis. HL-60 cells (100000-200000 cells per experiment) were washed twice with PBS (pH 7.2), and incubated in 300 μL PBS (pH 7.2) at 37° C. for 20 min. Streptolysin O (250 U), 28S rRNA green STAR (200 nM) and 28S rRNA TPP-DNA (2.0 μM) was added and the cell suspension incubated at 37° C. for 30 min. Sealing medium (1 mL; DMEM+0.2 mg/mL $CaCl_2$; 4° C.) was added and the cell suspension incubated at 4° C. for 1 h. The sealing medium was decanted and the cells resuspended in DMEM (0.5 mL). The live cell suspension was analyzed with a FACScan instrument (Becton Dickinson). Fluorescence signals were observed under the following conditions: excitation by argon laser, 488 nm; emission, 500-540 nm. Forward angle light scatter (FSC), side angle light scatter (SSC), and fluorescence data were recorded, and for each measurement, 20,000 events were stored. Data were analyzed with the FLOWJO program (Version 4.6.2, Tree Star, Ashland, Oreg.).

Kinetic analysis of 2-STAR and Q-STAR fluorescence activation. 2-STAR probes or Q-STAR probes (100 nM) and the corresponding template (100 nM, unless stated differently) were incubated at 37° C. in tris-borate buffer (70 mM, pH 7.55) containing $MgCl_2$ (10 mM). TPP-DNA (600 nM for mono TPP-DNA and 300 nM for dual TPP-DNA) was added and the fluorescence emission ($\lambda_{ex}=494$ nM; $\lambda_{em}=521$ nm) was measured as a function of time.

Analysis of thermal stability of 2-STAR and Q-STAR probes. A solution containing either the Q-STAR or 2-STAR probe (100 nM) and the template strand SE-DNA (100 nM) were incubated for 90 min without TPP-DNA in tris-borate buffer (70 mM, pH 7.55) containing $MgCl_2$ (10 mM) at the specified temperature. The solutions were cooled for 10 min on ice. Fluorescence signals were measured by 96-well microplate reader. As a reference for complete conversion, Q-STAR or 2-STAR probe (100 nM) was incubated for 5.5 h at 25° C. with SE-DNA (100 nM) and ms TPP-DNA (600 nM).

ABBREVIATIONS

MeCN is acetonitrile; DCM is methylene chloride; min is minutes; s is seconds; h is hours; TEA is triethylamine; EtOAc is ethyl acetate; FRET is fluorescence resonance energy transfer; Hex is hexane; DMF is N,N-dimethylformamide; THF is tetrahydrofuran; AcOH is acetic acid; Q-STAR is quenched Staudinger triggered α-azidoether release; 2-STAR is double quenched Staudinger triggered α-azidoether release; ATCC is American Type Culture Collection; PBS is phosphate buffered saline; HPLC is High Pressure Liquid Chromatography; SNP is single nucleotide polymorphism; PNA is peptide nucleic acid; LNA is locked nucleic acid; TPP is triphenylphosphine; CPG is controlled pore glass; PCR is polymer chain reaction; QUAL is quenched autoligation.

What is claimed is:

1. A selectively cleavable probe of structure (I):

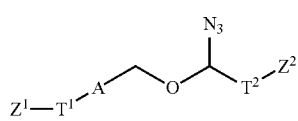

wherein A is an aromatic ring;
$T^1$ and $T^2$ are independently a tether; and
one of $Z^1$ and $Z^2$ is a a specific binding moiety and the other of $Z^1$ and $Z^2$ is a detection moiety.

2. The selectively cleavable probe of claim 1, wherein the compound is of structure (III):

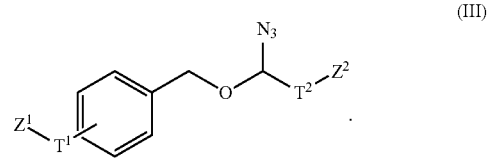

3. A selectively cleavable probe of one of structures (VIIIa) and (VIIIb):

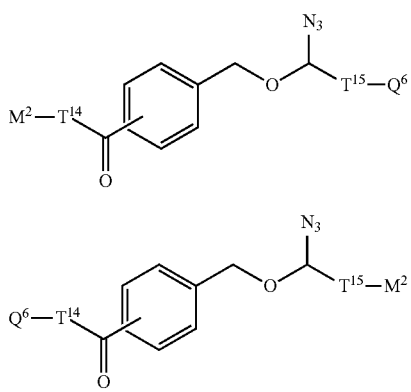

(VIIIa)

(VIIIb)

wherein T¹⁴ and T¹⁵ are independently a tether;
Q⁶ is a detection moiety; and
M² is a specific binding moiety.

4. The selectively cleavable probe of claim 3, wherein the probe is of structure (IX):

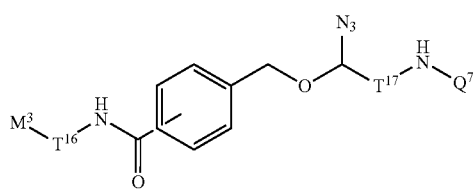

(IX)

wherein Q⁷ is a quencher;
M³ is a polynucleotide; and
T¹⁶ and T¹⁷ are independently a tether.

5. The selectively cleavable probe of claim 4, wherein: M³ comprises a fluorophore that is quenched by Q⁷.

6. The selectively cleavable probe of claim 1, wherein the detection moiety is selected from a fluorophore and a quencher.

7. The selectively cleavable probe of claim 1, wherein the specific binding moiety is selected from an antibody or fragment thereof, a polypeptide and a polynucleotide.

8. The selectively cleavable probe of claim 7, wherein the specific binding moiety is a polynucleotide of at least 6 bases in length and not more than about 100 bases in length.

9. The selectively cleavable probe of claim 8, wherein the detection moiety is a quencher, and said polynucleotide further comprises at least one fluorophore quenched by the detection moiety.

10. The selectively cleavable probe of claim 9, wherein the quencher is a dabsyl quencher.

11. The selectively cleavable probe of claim 3, wherein T¹⁴ and T¹⁵ are independently selected from one of the following structures, or a substituted version thereof:

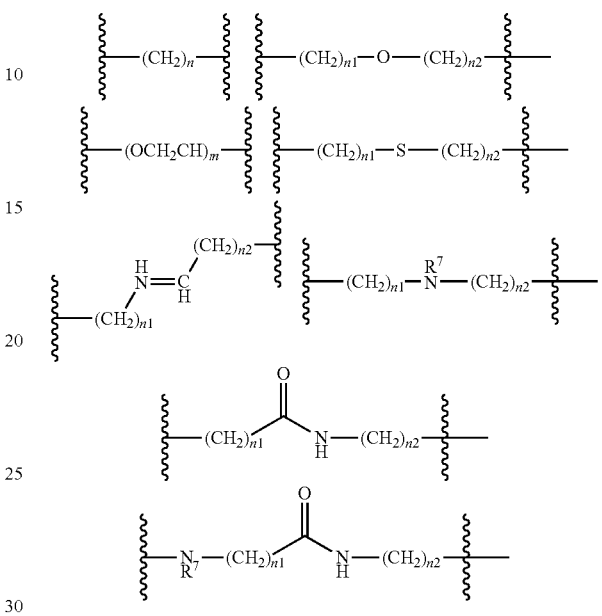

wherein:
n is an integer from 1 to 20;
$n_1$ and $n_2$ are independently selected integers from 1 to 20; where $n_1+n_2$ is about 20 or less;
m is an integer from 1 to 7; and
R⁷ is hydrogen or an alkyl.

12. The selectively cleavable probe of claim 3, wherein Q⁶ is selected from a fluorophore and a quencher.

13. The selectively cleavable probe of claim 3, wherein M² is selected from an antibody or fragment thereof, a polypeptide and a polynucleotide.

14. The selectively cleavable probe of claim 13, wherein M¹ is a polynucleotide of at least 6 bases in length and not more than about 100 bases in length.

15. The selectively cleavable probe of claim 14, wherein Q⁶ is a quencher, and said polynucleotide further comprises at least one fluorophore quenched by Q⁶.

16. The selectively cleavable probe of claim 15, wherein Q⁶ is a dabsyl quencher.

* * * * *

SEQUENCE LISTING

<160> NUMBER OF SEQ ID NOS: 14

<210> SEQ ID NO 1
<211> LENGTH: 8
<212> TYPE: DNA
<213> ORGANISM: Artificial Sequence
<220> FEATURE:
<223> OTHER INFORMATION: Synthetic Primer
<220> FEATURE:
<221> NAME/KEY: dimethylamino-azobenzene-sulfonyl
<222> LOCATION: (1)..(1)
<220> FEATURE:
<221> NAME/KEY: Fluorescein labeled deoxythymidine
<222> LOCATION: (3)..(3)
<220> FEATURE:
<221> NAME/KEY: Fluorescein labeled deoxythymidine
<222> LOCATION: (3)..(3)

<400> SEQUENCE: 1 agtcgaca                                                    8

<210> SEQ ID NO 2
<211> LENGTH: 8
<212> TYPE: DNA
<213> ORGANISM: Artificial Sequence
<220> FEATURE:
<223> OTHER INFORMATION: Synthetic Primer
<220> FEATURE:
<221> NAME/KEY: dimethylamino-azobenzene-sulfonyl
<222> LOCATION: (1)..(1)
<220> FEATURE:
<221> NAME/KEY: Fluorescein labeled deoxythymidine
<222> LOCATION: (3)..(3)
<220> FEATURE:
<221> NAME/KEY: Fluorescein labeled deoxythymidine
<222> LOCATION: (3)..(3)
<220> FEATURE:
<221> NAME/KEY: tetramethyl-6-carboxyrhodamine
<222> LOCATION: (8)..(8)

<400> SEQUENCE: 2 agtagaca                                                    8

<210> SEQ ID NO 3
<211> LENGTH: 8
<212> TYPE: DNA
<213> ORGANISM: Artificial Sequence
<220> FEATURE:
<223> OTHER INFORMATION: Synthetic Primer
<220> FEATURE:
<221> NAME/KEY: black hole quencher 2
<222> LOCATION: (1)..(1)
<220> FEATURE:
<221> NAME/KEY: Quasar 670
<222> LOCATION: (3)..(3)

<400> SEQUENCE: 3 agtagaca                                                    8

<210> SEQ ID NO 4
<211> LENGTH: 15
<212> TYPE: DNA
<213> ORGANISM: Artificial Sequence
<220> FEATURE:
<223> OTHER INFORMATION: Synthetic Primer
<220> FEATURE:
<221> NAME/KEY: triphenylphosphine
<222> LOCATION: (15)..(15)

<400> SEQUENCE: 4
agggcacaac ctcca                                           15

<210> SEQ ID NO 5
<211> LENGTH: 18
<212> TYPE: DNA
<213> ORGANISM: Artificial Sequence
<220> FEATURE:
<223> OTHER INFORMATION: Synthetic Primer

<400> SEQUENCE: 5
tcgtttacgg cgtggact                                        18

<210> SEQ ID NO 6
<211> LENGTH: 18
<212> TYPE: DNA
<213> ORGANISM: Artificial Sequence
<220> FEATURE:
<223> OTHER INFORMATION: Synthetic Primer

<400> SEQUENCE: 6
gctccggaag ccacgcct                                                    18

<210> SEQ ID NO 7
<211> LENGTH: 8
<212> TYPE: DNA
<213> ORGANISM: Artificial Sequence
<220> FEATURE:
<223> OTHER INFORMATION: Synthetic Primer
<220> FEATURE:
<221> NAME/KEY: two Dabsyl containing alpha-azidoethers
<222> LOCATION: (1)..(1)
<220> FEATURE:
<221> NAME/KEY: Fluorescein labeled deoxythymidine
<222> LOCATION: (3)..(3)
<220> FEATURE:
<221> NAME/KEY: Fluorescein labeled deoxythymidine
<222> LOCATION: (3)..(3)

<400> SEQUENCE: 7 agtcgaca                                                                8

<210> SEQ ID NO 8
<211> LENGTH: 8
<212> TYPE: DNA
<213> ORGANISM: Artificial Sequence
<220> FEATURE:
<223> OTHER INFORMATION: Synthetic Primer
<220> FEATURE:
<221> NAME/KEY: Two Dabsyl containing alpha-azidoethers
<222> LOCATION: (1)..(1)
<220> FEATURE:
<221> NAME/KEY: Fluorescein labeled deoxythymidine
<222> LOCATION: (3)..(3)
<220> FEATURE:
<221> NAME/KEY: Fluorescein labeled deoxythymidine
<222> LOCATION: (3)..(3)

<400> SEQUENCE: 8 agtagaca                                                                8

<210> SEQ ID NO 9
<211> LENGTH: 8
<212> TYPE: DNA
<213> ORGANISM: Artificial Sequence
<220> FEATURE:
<223> OTHER INFORMATION: Synthetic Primer
<220> FEATURE:
<221> NAME/KEY: Dabsyl containing alpha-azidoether
<222> LOCATION: (1)..(1)
<220> FEATURE:
<221> NAME/KEY: Fluorescein labeled deoxythymidine
<222> LOCATION: (3)..(3)
<220> FEATURE:
<221> NAME/KEY: Fluorescein labeled deoxythymidine
<222> LOCATION: (3)..(3)

<400> SEQUENCE: 9 agtagaca                                                                8

<210> SEQ ID NO 10
<211> LENGTH: 9
<212> TYPE: DNA
<213> ORGANISM: Artificial Sequence
<220> FEATURE:
<223> OTHER INFORMATION: Synthetic Primer
<220> FEATURE:
<221> NAME/KEY: triphenylphosphine
<222> LOCATION: (9)..(9)

```
<400> SEQUENCE: 10 caacctcca                                                                  9

<210> SEQ ID NO 11
<211> LENGTH: 9
<212> TYPE: DNA
<213> ORGANISM: Artificial Sequence
<220> FEATURE:
<223> OTHER INFORMATION: Synthetic Primer
<220> FEATURE:
<221> NAME/KEY: two triphenylphosphines
<222> LOCATION: (9)..(9)

<400> SEQUENCE: 11 caacctcca                                                                  9

<210> SEQ ID NO 12
<211> LENGTH: 15
<212> TYPE: DNA
<213> ORGANISM: Artificial Sequence
<220> FEATURE:
<223> OTHER INFORMATION: Synthetic Primer
<220> FEATURE:
<221> NAME/KEY: Two triphenylphosphines
<222> LOCATION: (15)..(15)

<400> SEQUENCE: 12
agggcacaac ctcca                                                          15

<210> SEQ ID NO 13
<211> LENGTH: 27
<212> TYPE: DNA
<213> ORGANISM: Artificial Sequence
<220> FEATURE:
<223> OTHER INFORMATION: Synthetic Primer

<400> SEQUENCE: 13
gatgtcgact tggaggttgt gcccttg                                             27

<210> SEQ ID NO 14
<211> LENGTH: 27
<212> TYPE: DNA
<213> ORGANISM: Artificial Sequence
<220> FEATURE:
<223> OTHER INFORMATION: Synthetic Primer

<400> SEQUENCE: 14
gatgtctact tggaggttgt gcccttg                                             27
```